(12) United States Patent
Yabuta et al.

(10) Patent No.: US 7,732,133 B2
(45) Date of Patent: Jun. 8, 2010

(54) SCREENING METHODS FOR BIOLOGICALLY ACTIVE LIGANDS

(75) Inventors: Naohiro Yabuta, Shizuoka (JP); Hideki Adachi, Shizuoka (JP); Yasushi Shimonaka, Shizuoka (JP); Kunihiro Hattori, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1104 days.

(21) Appl. No.: 10/333,103

(22) PCT Filed: Jul. 17, 2001

(86) PCT No.: PCT/JP01/06170

§ 371 (c)(1),
(2), (4) Date: Sep. 30, 2003

(87) PCT Pub. No.: WO02/06838

PCT Pub. Date: Jan. 24, 2002

(65) Prior Publication Data

US 2004/0091876 A1   May 13, 2004

(30) Foreign Application Priority Data

Jul. 17, 2000 (JP) ............................. 2000-221070
May 28, 2001 (JP) ............................. 2001-159032

(51) Int. Cl.
*G01Q 1/68* (2006.01)
*G01Q 33/53* (2006.01)
*G01N 33/566* (2006.01)
*C12P 21/04* (2006.01)
*C12N 15/00* (2006.01)

(52) U.S. Cl. ............................. 435/6; 435/7.1; 435/7.2; 435/69.7; 435/320.1; 436/501

(58) Field of Classification Search ........................ None
See application file for complete search history.

(56) References Cited

U.S. PATENT DOCUMENTS 4,859,609 A 8/1989 Dull et al.
5,574,136 A * 11/1996 Nagata et al. ............... 530/350

FOREIGN PATENT DOCUMENTS

| JP | 62-272990 A | 11/1987 |
| JP | 6-510531 A | 11/1994 |
| JP | 8-508889 A | 9/1996 |
| WO | WO 93/04373 | 3/1993 |
| WO | WO 94/29458 | 12/1994 |
| WO | WO9641169 A1 | 12/1996 |
| WO | WO 01/25797 * | 9/2000 |

OTHER PUBLICATIONS

Friedrich et al., A two-step selection approach for the identification of ligand-binding determinants in cytokine receptors, 1998, Analytical Biochemistry, vol. 268, pp. 179-186.*
Takahashi et al., Swapping between Fas and granulocyte colony-stimulating factor receptor, 1996, Journal Biological Chemistry, vol. 271, Issue 29, pp. 17555-17560.*
Delrieu et al., IL-6 promoter is modulated by the 24 kDa FGF-2 isoform fused to the hormone binding domain of the oestrogen receptor, Cytokine, vol. 12, Issue 7, pp. 1110-1114.*
Bork et al., Go hunting in sequence databases but watch out for the traps, 1996, Trends in Genetics, vol. 12, pp. 425-427.*
Bork, Powers and Pitfalls in Sequence Analysis: the 70% hurdle, 2000, Genome Research, vol. 10, pp. 398-400.*
Brenner, Errors in genome annotation, 1999, Trends in Genetics, vol. 15, pp. 132-132.*
Doerks et al., Protein annotation: detective work for function prediction, 1998, Trends in Genetics, vol. 14, pp. 248-250.*
Ngo et al., The protein folding problem and tertiary structure prediction,1994, pp. 492-495.*
Skolnick et al., From genes to protein structure and function: novel applications of computational approaches in the genomic era, 2000, Trends in Biotech, vol. 18, Issue 1, pp. 34-39.*

(Continued)

*Primary Examiner*—Robert Landsman
*Assistant Examiner*—Ian Dang
(74) *Attorney, Agent, or Firm*—Fish & Richardson P.C.

(57) ABSTRACT

In the case when there are two objective biological activities, and the aim is to isolate a compound having at least one biological activity, the present inventors developed an assay method wherein a common detection marker is utilized for separately detecting the presence or absence of each of the biological activities. The present inventors discovered that a compound having at least one of two or more distinct biological activities can be efficiently and conveniently detected by simultaneously assaying at least one test sample or more by the above-mentioned method. Furthermore, for a test sample that proved to be positive by the detection method, they found that it is possible to efficiently and conveniently screen for a test sample having an objective specific biological activity by combining with a method wherein an individual activity of a test sample can be detected to specify the biological activity.

14 Claims, 20 Drawing Sheets

OTHER PUBLICATIONS

Smith et al., The challenge of genome sequence annotation or "the devil is in the details", 1997, Nature Biotechnology, vol. 15, pp. 1222-1223.*

Wells et al., Addivity of mutational effects in proteins, 1990, Biochemistry, vol. 29, pp. 8509-8517.*

Geiger et al., "Integrated src kinase and costimulatory activity enhances signal transduction through single-chain chimeric receptors in T lymphocytes," Blood, 98(8):2364-2371 (2001).

Seldin et al., "The Human IL4 Receptor Shares a Critical Signal Transduction Domain with Other Cytokine Receptors" J. Cell. Biochem. Suppl., Keystone Symposium on Hematopoiesis, Abstract No. M328, p. 89 (1992).

Ishizaka-Ikeda et al., "Signal transduction mediated by growth hormone receptor and its chimeric molecules with the granulocyte colony-stimulating factor receptor", *Proc. Natl. Aca. Sci. USA*. vol. 90, pp. 123-127 (1993).

Kammer et al., "Homodimerization of interleukin-4 receptor alpha chain can induce intracellular signaling." J. Biol. Chem. 271(39):23634 (1996).

Aritomi et al., "Atomic structure of the GCSF-receptor complex showing a new cytokine-receptor recognition scheme," Nature, 401(6754):713-717 (1999).

Boehm et al., "Rac-dependent anti-apoptotic signaling by the insulin receptor cytoplasmic domain," J. Biol. Chem,. 274(40):28632-28636 (1999).

Boileau and Czajkowski, "Identification of transduction elements for benzodiazepine modulation of the GABA(A) receptor: three residues are required for allosteric coupling," J. Neurosci., 19(23):10213-10220 (1999).

Jorrissen et al., "Characterization of a comparative model of the extracellular domain of the epidermal growth factor receptor," Protein Sci., 9(2):310-324 (2000).

Koay and Sartorelli, "Functional differentiation signals mediated by distinct regions of the cytoplasmic domain of the granulocyte colony-stimulating factor receptor," Blood, 93(11):3774-84 (1999).

Mikhailenko et al., "Functional domains of the very low density lipoprotein receptor: molecular analysis of ligand binding and acid-dependent ligand dissociation mechanisms," J. Cell. Sci., 112 (Pt 19):3269-3281 (1999).

Muthukumaran et al., "Chimeric erythropoietin-interferon gamma receptors reveal differences in functional architecture of intracellular domains for signal transduction," J .Biol. Chem., 272(8):4993-9 (1997).

Pelczar et al., "A conditional version of the Ets transcription factor Erm by fusion to the ligand binding domain of the oestrogen receptor," Biochem. Biophys. Res. Commun., 239(1):252-256 (1997).

Prigent and Gullick, "Identification of c-erbB-3 binding sites for phosphatidylinositol 3'-kinase and SHC using an EGF receptor/c-erbB-3 chimera," EMBO J., 13(12):2831-41 (1994).

Rogerson et al., "Structural determinants of aldosterone binding selectivity in the mineralocorticoid receptor," J. Biol. Chem., 274(51):36305-11 (1999).

Scheer et al., "Structure-function relationships of the alpha1b-adrenergic receptor," Eur. Urol., 36 (Suppl 1):11-16 (1999).

Ueno et al., "An epidermal growth factor receptor-leukocyte tyrosine kinase chimeric receptor generates ligand-dependent growth signals through the Ras signaling pathway," J. Biol. Chem., 270(34):20135-42 (1995).

Villmann et al., "Kainate binding proteins possess functional ion channel domains," J. Neurosci., 17(20):7634-43 (1997).

Yeagle et al., "Structure determination of the fourth cytoplasmic loop and carboxyl terminal domain of bovine rhodopsin," Mol. Vis., 2:12 (1996).

* cited by examiner

SCREENING METHODS FOR BIOLOGICALLY ACTIVE LIGANDS

CROSS REFERENCE TO RELATED APPLICATIONS

The present application is a national phase application under 35 U.S.C. Section 371 filed from International Patent Application PCT/JP01/06170, filed 17 Jul. 2001, which claims priority to Japanese patent application Serial. No. JP 2000-221070, filed 17 Jul. 2000 and to Japanese patent application Serial. No. JP 2001-159032, filed May 28, 2001. The contents of these applications are incorporated herein by reference in their entirety.

TECHNICAL FIELD

This invention relates to efficient screening methods for biologically active substances that bind receptors.

BACKGROUND ART

Hematopoietic factors represented by erythropoietin (EPO) and granulocyte-colony stimulating factor (G-CSF) have already been developed as pharmaceutical agents, and have been utilized for the treatment of various diseases. Cytokines, such as interferon, and hormones, including insulin and growth hormone, are also commercially available as pharmaceutical agents. Most of the biologically active proteins used as pharmaceutical agents have been produced by genetic engineering techniques. Low molecular weight compounds are being screened as the next-generation drugs replacing biologically active proteins. For instance, if it was possible to find low molecular weight compounds having the same activities as biologically active proteins, such compounds will be useful as pharmaceutical agents, since they may be orally administered. Therefore, there is a need to develop efficient methods for screening low molecular weight compounds that have biological activities similar to naturally existing ligands.

Several screening methods are already known. For example, when screening for a ligand of a receptor whose amino acid sequence and function are known, there is a method in which a chimeric receptor comprising the intracellular domain of a receptor with a known function and the extracellular domain of a receptor of interest is prepared, and the chimeric protein is used to screen for a ligand of the receptor of interest (Ishizaka-Ikeda, E., Pro. Natl. Acad. Sci. USA (1993) 90, p123-127; U.S. Pat. No. 4,859,609 and U.S. Pat. No. 5,030,576). Using the insulin receptor as the extracellular domain and the EGF receptor as the intracellular domain, these US patents describe a method that assays in a cell-free system chimeric receptor phosphorylation induced by the binding of a ligand. A method using a chimeric receptor that consists of the extracellular domain of the EGF receptor and the intracellular domain of the EPO receptor, has also been reported (WO94-29458). These approaches may also be applicable to the screening of ligands for an orphan receptor, whose natural ligand is not yet known.

However, in each of these screening methods, only one kind of receptor is used as the receptor of interest, and one screening can only detect the effect a test sample has on that single receptor. Therefore, in order to assay the effect on several receptors, the same number of screenings as that of receptors of interest is required. Also, these approaches are inefficient for a preliminary screening of a vast number of test samples that have different structures and whose activities are unconfirmed, since activities of most ligands cannot be detected. It is, therefore, necessary to develop a method that can efficiently and rapidly screen a vast number of test samples.

DISCLOSURE OF THE INVENTION

The present invention provides an efficient method of screening for substances that bind biologically active receptors.

In the case when there are two or more objective biological activities, and the aim is to isolate a compound having at least one of the biological activities, exhaustive research conducted by the present inventors led to the development of an assay method wherein a common detection marker is utilized for separately detecting the presence or absence of each of the biological activities. The present inventors completed the invention by discovering that a compound having at least one of two or more distinct biological activities can be efficiently and conveniently detected by simultaneously assaying at least one test sample or more by the above-mentioned method. Furthermore, for a test sample that proved to be positive by the detection method, they found that it is possible to efficiently and conveniently screen for a test sample having an objective specific biological activity by combining with a method wherein an individual activity of a test sample can be detected to specify the biological activity.

Specifically, the present invention provides:
(1) a method for simultaneously detecting two or more distinct activities, wherein said method comprises the steps of:
   (i) determining in advance, a detection marker common to said activities,
   (ii) preparing a detection method that can detect each of said two or more distinct activities using said common detection marker, and
   (iii) simultaneously detecting said activities using said detection method;
(2) a method for selecting a test sample that has at least one of two or more distinct activities, wherein said method comprises the steps of:
   (i) determining in advance, a detection marker common to said activities,
   (ii) preparing a detection method that can detect each of said two or more distinct biological activities using said common detection marker, and
   (iii) simultaneously detecting at least one of the biological activities of a test sample using said detection method;
(3) a method of screening for a ligand that can bind to at least one of two or more kinds of receptors, wherein said method comprises the steps of:
   (i) obtaining two or more kinds of receptors comprising (a) a common signal-transducing domain, and (b) a domain other than the signal-transducing domain, wherein said domain derives from the same receptor from which the common domain of (a) is derived and/or a different receptor,
   (ii) contacting a test sample with said two or more kinds of receptors, and
   (iii) detecting the biological activity of said test sample;
(4) the method according to (3), wherein said step (i) obtains a cell expressing two or more kinds of receptors comprising (a) a common signal-transducing domain, and (b) a domain other than the signal-transducing domain, wherein said domain derives from the same receptor from which the common domain of (a) is derived and/or a different receptor;

(5) the method according to (3), wherein said step (i) obtains two or more kinds of cells that express a receptor comprising (a) a common signal-transducing domain, and (b) a domain other than the signal-transducing domain, wherein said domain derives from the same receptor from which the common domain of (a) is derived and/or a different receptor;

(6) a method according to any one of (3) to (5), wherein said signal-transducing domain and/or said domain other than the signal-transducing domain is derived from a cell membrane receptor;

(7) a method according to any one of (3) to (5), wherein said signal-transducing domain and/or said domain other than the signal-transducing domain is derived from a nuclear receptor;

(8) the method according to (6), wherein said domain other than the signal-transducing domain is the extracellular domain, of a cell membrane receptor, or a portion thereof;

(9) the method according to (6), wherein said domain other than the signal-transducing domain is a ligand-binding domain of a cell membrane receptor;

(10) the method according to (6), wherein said signal-transducing domain and/or said domain other than the signal-transducing domain is derived from a receptor belonging to a receptor family selected from the group consisting of the hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, cell adhesion receptor family, and hormone receptor family;

(11) the method according to (6), wherein said signal-transducing domain and/or said domain other than the signal-transducing domain is derived from the following receptors: human or mouse erythropoietin (EPO) receptor, human or mouse granulocyte-colony stimulating factor (G-CSF) receptor, human or mouse thrombopoietin (TPO) receptor, human or mouse receptor, human or mouse Flt-3, human or mouse platelet-derived growth factor (PDGF) receptor, human or mouse interferon (IFN)-α or -β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, or human or mouse ciliary neurotrophic factor (CNTF) receptor;

(12) the method according to (11), wherein said signal-transducing domain derives from mouse G-CSF receptor;

(13) the method according to (3), wherein in step (ii), two or more kinds of cells expressing said receptors are mixed and contacted with the test sample;

(14) the method according to any one of (4) to (13), wherein said cell(s) is a transformed cell(s);

(15) the method according to (14), wherein said cell(s) is derived from a cytokine-dependent cell;

(16) the method according to (15), wherein said transformed cell(s) is derived from Ba/F3 cells or FDC-P1 cells;

(17) a method according to (2) or (3), wherein in step (iii), an agonist or antagonist activity of the test sample is detected;

(18) the method according to (2) or (3), wherein in step (iii), the biological activity of the test sample is measured by using a cell-free detection system;

(19) the method according to (2) or (3), wherein in step (iii), the biological activity of the test sample is measured by using a cell-based detection system;

(20) the method according to (19), wherein in step (iii), the biological activity of the test sample is measured using a phenotypic change in the cell;

(21) the method according to (20), wherein said phenotypic change is a quantitative and/or qualitative change of a cell surface antigen;

(22) the method according to (20), wherein said phenotypic change is a change in proliferation activity;

(23) the method according to (3), which method further comprises the step of measuring the biological activity of a test sample by contacting it with one of said two or more receptors obtained in (i) in order to determine the specificity of the test sample towards the receptor;

(24) a cell that expresses two or more kinds of receptors comprising (a) a common signal-transducing domain, and (b) a domain other than the signal-transducing domain, wherein said domain derives from the same receptor from which the common domain of (a) is derived and/or a different receptor;

(25) a kit for screening a substance or ligand that binds to at least one of two or more kinds of receptors, wherein said kit comprises one of (a) to (c):

(a) two or more kinds of receptors comprising (a) a common signal-transducing domain, and (b) a domain other than the signal-transducing domain, wherein said domain derives from the same receptor from which the common domain of (a) is derived and/or a different receptor;

(b) DNA encoding two or more kinds of receptors comprising (a) a common signal-transducing domain, and (b) a domain other than the signal-transducing domain, wherein said domain derives from the same receptor from which the common domain of (a) is derived and/or a different receptor;

(c) a cell expressing two or more kinds of receptors comprising (a) a common signal-transducing domain, and (b) a domain other than the signal-transducing domain, wherein said domain derives from the same receptor from which the common domain of (a) is derived and/or a different receptor;

(26) a substance or ligand isolated by the screening according to (2) or (3); and

(27) a pharmaceutical composition comprising the substance or ligand according to (26).

The present invention converted a method that detected activities using different markers into a test method that detects activities using a predetermined detection marker. Thereby, the present invention developed a method that simultaneously detects two or more distinct activities having a common detection marker. The two or more activities are not restricted to any particular activities if the activities include several, distinct activities, but are preferably biological activities. "Biological activities" mean activities that can influence or cause quantitative and/or qualitative changes in a living body, tissue, cell, protein, DNA, RNA, etc. The two or more different biological activities can be any combinations of any biological activities if the activities can be detected by using a common detection marker. Biological activities include, cytokine activity, enzyme activity, transcription activity, membrane transport activity, and binding activity, etc. Examples of enzyme activities are, proteolytic activity, phosphorylation/dephosphorylation activity, redox activity, transfer activity, nucleic acid degradation activity, and dehydration activity. Furthermore, antigen-antibody reaction, and binding and/or activation of cell adhesion factors are examples of binding activities. It is preferable to use two or more biological activities of the same category, since it is relatively easy to design a detection method using a common marker.

The two or more activities can be measured by using different markers for each of the activities. However, the predetermined detection marker used in the present invention, is one of the distinct markers used to assay the two or more activities, or is a marker that is different from those markers. As detection markers used for the methods of the present invention, any markers can be utilized if quantitative and/or qualitative changes can be measured. For example, markers for cell-free or cell-based assays, tissue-specific markers, and organism-specific markers can be used. As markers for cell-free systems, enzyme reactions and quantitative and/or qualitative changes in proteins, DNA and RNA can be used. As an enzyme reaction, for instance, an amino acid transfer reaction, a glycosyl transfer reaction, a dehydration reaction, a dehydrogenation reaction, and a substrate-cleaving reaction can be used. Furthermore, protein phosphorylation, dephosphorylation, dimerization, multimerization, degradation, and dissociation, and such, and DNA or RNA amplification, digestion and elongation can also be used. For example, downstream protein phosphorylation in signal transduction pathways can be used as a detection marker. As markers for cell-based systems, changes in cellular phenotype, for example, quantitative and/or qualitative changes-in cellular products, cell proliferation activity changes, morphological changes, changes in cellular characteristics, and such can be used. As cellular products, secretory proteins, cell-surface antigens, intracellular proteins, mRNA, and such can be used. As cellular morphological changes, changes in: the formation and/or number of cellular protrusions; the degree of cell flatness; cellular elongation or the ratio between cellular length and width; cell-size; intracellular structure; heterogeneity or homogeneity in the cell population; cell density; and such can be used. These morphological changes can be recognized by microscopic observations. As changes in cellular characteristics, changes in anchorage dependency, cytokine dependency, hormone dependency, drug resistance, cell motility, cell migration activity, pulsatility, intracellular substance, and such can be used. Cell motility can be assayed by measuring cell invasion and migration activities. As changes in intracellular substances, enzyme activities, mRNA quantity, amounts of intracellular signal transducers such as $Ca^{2+}$ and cAMP, protein contents, and such can be used. To select a compound having an agonist activity for a cell-membrane receptor, a change in cell growth activity induced by the stimulation of the receptor can be used as a marker. For tissues, functional changes in respective tissues can be used as detection markers. As markers for living organisms, changes in tissue weight, changes in the blood system, for example, changes in blood cell counts, protein contents, enzyme activities, electrolyte amounts; as well as changes in the circulatory system (for example, changes in blood pressure and heart rate, etc.) can be used.

These detection markers are not restricted, and luminescence, coloring, fluorescence, radio activity, fluorescence polarity, surface plasmon resonance signal, time-resolved fluorescence, mass, absorption spectra, light scattering, and fluorescence resonance energy transfer, and such can be used. These methods are well known to those skilled in the art, and one can select an appropriate method for one's purpose. For example, absorption spectra, luminescence, and fluorescence can be measured by using generally used photometers and plate readers, luminometers, and fluorometers, respectively. Mass can be measured by using a mass spectrometer. Radiation can be measured by using an instrument such as a gamma counter depending on the type of radioactive ray; fluorescence polarity can be measured by using BEACON (Takara Shuzo Co., Ltd); surface plasmon resonance signals can be measured by using BIACORE; time-resolved fluorescence, fluorescence resonance energy transfer, and such can be measured by using ARVO, etc. Flow cytometers and such can also be used for the measurement. Each of these methods can be used to assay two or more detection markers, and may also be used for the simultaneous and/or continuous assay of two or more different markers if such an assay would be convenient. For instance, a fluorometer can simultaneously measure fluorescence and fluorescence resonance energy transfer.

One embodiment of the methods according to the present invention is a screening method for the selection of compounds having at least one of two or more distinct biological activities. For example, the method can be used for the selection of a ligand that can bind one of two or more different receptors of interest.

In the present invention, "ligand" means a substance that has an activity to bind a receptor, and that is able to induce biological activities through the binding to the receptor. Among the ligands, a substance that is produced by a living organism and that has a biological activity in an organism is called a natural ligand.

In the methods of the present invention, any sample whose biological activity is to be detected can be used as a test sample. Examples of test samples are cell extracts, cell culture supernatants, microorganism fermentation products, marine organism extracts, plant extracts, purified or crude proteins, peptides, non-peptide compounds, synthetic low-molecular-weight compounds, and natural compounds; but are not limited to these examples.

Any kind of receptor molecule can be used in the methods of the present invention, if upon ligand binding, the receptor can induce changes in a characteristic of a detection marker. For example, cell membrane receptors, nuclear receptors, and intracellular receptors can be used. Cell membrane receptors are receptors expressed on the cell surface, and upon ligand binding to the extracellular domain of the receptor, can transmit a signal into the cell and induce some biological change. Specifically, receptor molecules belonging to the following families can be used; the hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, cell adhesion receptor family, and hormone receptor family, etc.

Characteristics of the receptors of these families can be found in various literatures, for example, in the following: Cooke BA., King RJB., van der Molen HJ. ed. New Comprehesive Biochemistry Vol.18B "Hormones and their Actions Part II" pp.1-46 (1988) Elsevier Science Publishers BV., New York, USA; Patthy L. (1990) Cell, 61: 13-14.; Ullrich A., et al. (1990) Cell, 61: 203-212.; Massagul J. (1992) Cell, 69: 1067-1070.; Miyajima A., et al. (1992) Annu. Rev. Immunol., 10: 295-331.; Taga T. and Kishimoto T. (1992) FASEB J., 7: 3387-3396.; Fantl WI., et al. (1993) Annu. Rev. Biochem., 62: 453-481.; Smith CA., et al. (1994) Cell, 76: 959-962.; Flower DR. (1999) Biochim. Biophys. Acta, 1422: 207-234.; Miyasaka M. ed. Cell Technology, Handbook Series "Handbook for adhesion factors" (1994) Shujunsha, Tokyo, Japan, etc. As specific receptors belonging to the families, the following molecules can preferably be used in the present invention: for example, human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (rFN)-α or -β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor. Sequences of these receptors are well known (hEPOR: Jones, SS. et al. (1990) Blood, 76, 31-35; mEPOR: D'Andrea, AD. et al. (1989) Cell 57, 277-285.; hG-CSFR: Fukunaga, R. et al. (1990) Proc. Natl. Acad. Sci. USA. 87, 8702-8706.; mG-CSFR: Fukunaga, R. et al. (1990) Cell 61, 341-350.; hTPOR: Vigon, I. et al. (1992) 89, 5640-5644.; mTPOR: Skoda, RC. et al. (1993) 12, 2645-2653.; hInsR: Ullrich, A. et al. (1985) Nature 313, 756-761.; hFlt-3: Small, D. et al. (1994) Proc. Natl. Acad. Sci. USA. 91, 459-463.; hPDGFR: Gronwald, RGK. et al. (1988) Proc. Natl. Acad. Sci. USA. 85, 3435-3439.; hIFNα/β R: Uze, G. et al. (1990) Cell 60, 225-234.; and Novick, D. et al. (1994) Cell 77, 391-400). Nuclear receptors are receptors that can bind specific DNA sequences following ligand binding, and regulate the transcription activity of mRNA. Examples are, the steroid and retinoid X receptor families, and such. The steroid receptor family includes the glucocorticoid receptor, mineral corticoid receptor, progesterone receptor, androgen receptor, and estrogen receptor. The retinoid X receptor family includes retinoic acid receptor, thyroid hormone receptor, and vitamin D3 receptor. Intracellular receptors are receptors that exist inside the cell, and induce biological activities in the cell, upon binding to various ligands.

In a method for selecting a substance or ligand that can bind any one of two or more receptors of interest, a common functional domain of the receptors can be used for developing a method for detecting the common marker. A functional domain is a receptor domain required for the induction of a biological activity, and is usually a domain distinct from the ligand-binding domain. When receptors are cell membrane receptors capable of binding to secretory proteins such as cytokines or hematopoietic factors, an intracellular domain of the receptor, preferably the signal-transducing domain, can be used as the functional domain. Therefore, a method utilizing a common detection marker can be developed by constructing chimeric receptors having a common signaling domain with the same amino acid sequence, and different extracellular domains. As a marker for cell-free systems, the formation of multimers, preferably dimers, of the receptors can be used. In the case of cytokine receptors, it is known that signal transduction is induced by ligand-induced dimerization or multimerization of the receptors. Hence, receptor dimerization or multimerization can be used as a detection marker. For example, detection can be done by directly immobilizing a receptor onto an immunoplate, or by immobilizing a biotinylated receptor onto an avidin-immobilized plate, mixing a test sample and a radio-labeled receptor, and detecting a test sample that promotes the binding of the radio-labeled receptor to the immobilized receptor by scintillitant proximal assay (SPA) (WO99-53313; or Qureshi, S A, et al., Proc. Natl. Acad. Sci. USA, (1999) 96, p12156-12161). Phosphorylation, dephosphorylation, degradation, and such of receptor molecules can also be appropriately used as detection markers. Phosphorylation or dephosphorylation reaction can be measured by a usual method well known to those skilled in the art or by using a commercially available kit. Changes in cell growth activity can be used as the detection marker for a cell culture system. Changes in cell growth activity can be measured by the MTT method or a method using tritium-labeled thymidine. Quantitative and/or qualitative changes in cell surface antigens can be detected by detecting the bound amount of a fluorescence-labeled specific antibody, using a flow cytometer or fluorescence microscope. Furthermore, depending on downstream signaling, phosphorylation of substrate proteins, and changes in the concentration of second messengers such as cAMP and $Ca^{2+}$ can also be measured as detection markers. These methods are already well known, and the detection can also be conducted by using generally used methods and kits. Reporter gene assays using activity of, for example, luciferase, chloramphenicol acetyltransferase, and β-galactosidase can also be utilized for the detection of downstream gene expression regulated by the chimeric receptors. As described above, screening by simultaneous and/or continuous measurement of these multiple distinct markers is one of the efficient and simple screening methods provided by the present invention. Due to the ease in detection, cell-based detection markers are preferable, and especially preferable is a method that uses cell growth activity as a detection marker.

Furthermore, in the methods of the present invention, the signal-transducing domain derived from one of the two or more receptors of interest can be used as it is. The other receptor can be chimeric comprising the above-mentioned signal-transducing domain and a different extracellular domain. Chimeric receptors may have partial sequences of two or more distinct receptors. Alternatively, they may comprise the whole receptor of one of two or more distinct receptors, plus a whole completely different receptor, or a portion thereof. For example, chimeric receptors can have the extracellular domain of a cell membrane receptor and the intracellular domain of another cell membrane receptor, and can also have the ligand-binding domain of a nuclear receptor and the DNA-binding domain of another nuclear receptor. By using multiple chimeric receptors having a common DNA-binding domain and a different ligand-binding domain, the effect on the multiple receptors can be simultaneously detected. Furthermore, chimeric receptors having the whole molecule or intracellular domain of a cell membrane receptor and the whole molecule or ligand-binding domain of an intracellular receptor can also be used. In this case, the intracellular domain of this chimeric receptor derives from a cell membrane receptor and the extracellular domain derives from an intracellular receptor. Therefore, a ligand inducing multimerization, preferably dimerization, by binding to the intracellular receptor, can be detected by using a detection marker induced by the multimerization or dimerization of the cell membrane receptor used.

The extracellular domain used for the chimeric receptor of a cell membrane receptor, may be any domain other than the signal-transducing domain of the receptor, and may be the whole extracellular domain, or a portion thereof. The whole extracellular domain may preferably be used as it may properly reflect the biological activity. In the case of using partial domains of a receptor's extracellular domain, the ligand-binding domain, or a membrane-proximal domain having 20 or more amino acid residues, preferably 50 or more residues, or more preferably 100 or more residues can be used for the construction of the chimeric receptor. As the extracellular domain utilized for the construction of a chimeric receptor, any partial sequence can be used, as long as the multimerization, preferably, dimerization, of the signal-transducing domain is induced, and changes in the detection marker are also induced. In this case, there may a substitution, deletion, insertion, or addition to the amino acids constituting the extracellular domain. One method well known to those skilled in the art for preparing functionally equivalent proteins is to introduce mutations into proteins. For example, those skilled in the art can construct such a protein by using site-directed mutagenesis (Hashimoto-Gotoh, T. et al. (1995) Gene 152, 271-275; Zoller, M J, and Smith, M.(1983) Methods Enzymol. 100, 468-500; Kramer, W. et al. (1984) Nucleic Acids Res. 12, 9441-9456; Kramer W, and Fritz H J (1987) Methods Enzymol. 154, 350-367; Kunkel, T A (1985) Proc Natl Acad Sci USA. 82, 488-492; Kunkel (1988) Methods Enzymol. 85, 2763-2766), etc.

It is thought that the number of amino acid residues mutated in such a mutant protein is usually 50 or less, preferably 30 or less, more preferably 20 or less, even more preferably 10 or less, further more preferably 5 or less, or even further more preferably 3 or less.

It is preferable to mutate an amino acid residue into one that allows the properties of the amino acid side-chain to be conserved. Examples of properties of amino acid side chains include: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chain (R, K, H); and aromatic-containing side-chains (H, F, Y, W) (The letters within parentheses indicate the one-letter codes of amino acids).

It is well known that a protein having deletion, addition, and/or substitution of one or more amino acid residues in the sequence of the protein can retain the original biological activity (Mark, D. F. et al. Proc. Natl. Acad. Sci. U.S.A. 81:5662-5666 (1984); Zoller, M. J. and Smith, M. Nucleic Acids Res. 10:6487-6500 (1982); Wang, A. et al. Science 224:1431-1433; Dalbadie-McFarland, G. et al. Proc. Natl. Acad. Sci. U.S.A. 79:6409-6413 (1982)).

The transmembrane domain utilized for the construction of a chimeric receptor can derive from the receptor from which the extracellular or intracellular domain derived. Furthermore, the transmembrane domain can derive from the both these receptor molecules utilized for the construction of the chimeric receptor, or can also derive from cell membrane receptors other than those utilized for the construction. Since multiple chimeric receptors can easily be made, the transmembrane domain of chimeric receptors may preferably derive from receptors used as the intracellular domain for the construction of the chimeric receptor.

The intracellular domains of chimeric receptors used in the present invention are not restricted, as long as ligand-induced changes in phenotypes can be detected. For example, the intracellular domain of G-CSF, EPO, EGF, or TPO receptor can be used, utilizing as a marker the cell growth activity induced by stimulation of these receptors. For example, a chimeric receptor having the extracellular domain of the growth hormone receptor and the intracellular domain of the G-CSF receptor, has been shown to induce cell growth depending on growth hormone stimulation (Fuh, G. Science (1992) 256, 1677-1680).

It is preferable to use the signaling domain of mouse G-CSF receptor for the construction of chimeric receptors, as the structure and function of the receptor have been studied in detail. The mouse G-CSF receptor consists of 813 amino acid residues, and a single transmembrane domain separates the extracellular and intracellular domains (Fukunaga, R. Cell (1990) 61, 341-350). It has also been shown that when the G-CSF receptor is expressed in FDC-P1, a myelocyte precursor cell line, and Ba/F3, a pro-B cell line, the expressed receptor can transmit a growth-stimulating signal, and a G-CSF-dependent proliferative activity is seen. Furthermore, it has also been shown that the intracellular 76 amino acid residues of the G-CSF receptor are essential for the transmission of the G-CSF growth stimulation (Fukunaga, R. EMBO J. (1991) 10, 2855-2865). By constructing a chimeric receptor containing the 76 amino acid residues as the signal-transducing domain and expressing the chimeric receptor in Ba/F3 cells, it is possible to use cell growth activity as a detection marker.

It has been shown that the deletion of downstream amino acid residues after the 716th residue of human G-CSF receptor restricts the internalization of the receptor, resulting in enhanced signal transduction efficiency following G-CSF stimulation due to the increased number of receptors on the cell surface (Melissa G., Blood (1999) 93, 440-446). This deleted domain contains a motif called Box3, which is presumed to be crucial for the receptor's internalization. Box1 and box2 essential for the signal transduction are however retained. Therefore, it can be presumed that even in the mouse G-CSF receptor, it may be possible to enhance the signal transduction efficiency following G-CSF stimulation by deleting the domain containing box3, but not box2.

Any cell line can be used to express a chimeric receptor, if the cell line can respond to the ligand only when the chimeric receptor is expressed, and if the ligand does not cause phenotypic changes to the cell lines in which the chimeric receptor is not expressed. When cell growth activity is utilized as a detection marker, it is preferable to use cell lines that die in the absence of the ligand in order to increase detection sensitivity. Particularly, cytokine-dependent cell lines are useful, since they can easily be passaged. For example, IL-2-dependent CTLL-2 cells, IL-3-dependent 32D cells, FDC-P1 cells and Ba/F3 cells can be used. These cell lines have the characteristic of dieing in day-2 or -3 after removing cytokines, such as IL-2 or -3 required for the growth, from the culture media. It is preferable to use FDC-P1 or Ba/F3 cells expressing a chimeric receptor comprising the intracellular domain of mouse G-CSF receptor. As hosts used in the methods of the present invention, not only animal cell lines but also yeast and *Escherichia coli* can be used. When ligand-mediated receptor dimerization is used for the detection marker, for example, the two-hybrid system utilizing chimeric receptors can be used. Specifically, by constructing a gene the encodes a chimeric receptor comprising the activation domain of yeast GAL4 and a receptor, or a chimeric receptor comprising the ligand-binding domain of GAL4 and a receptor, and expressing in yeast, the expression of a reporter gene in the yeast can be monitored in culture in the presence of test samples. The activities of many different substances on multiple cell membrane receptors can simultaneously be assayed by constructing multiple chimeric receptors from different receptors.

Furthermore, the cell lines of the present invention can be modified to improve the screening sensitivity. The sensitivity of the cells can be increased, for example, by expressing chimeric receptor molecules using an appropriate regulatory domain and a polyadenylation signal so that the expression of chimeric receptor molecules will increase, or by replacing the mRNA instability signals with stable ones. Chimeric receptor genes in which the domain flanking the initiation codon has been modified into the Kozak's consensus sequence (CCACC) may also be used. Furthermore, it is possible to easily obtain cell lines with a high expression by combining with a suitable selection marker. For example, well known is a method in which dihydrofolate reductase (DHFR) is used as a marker for cell lines that lack the DHFR gene, and methotrexate is used to inhibit DHFR to obtain a cell line that highly expresses an objective gene. Also known is a method that uses the thymidine kinase gene that lacks the promoter as a selection marker to select a cell line that highly expresses a gene of interest. Furthermore, for example, it is also possible to specifically select cells showing a high expression by using a cell sorter after binding a florescence-labeled anti-receptor antibody or coexpressing with green fluorescence protein (GFP), etc. Modification of the receptor's metabolic process may also provide a highly sensitive detection system. For example, it is known that mouse G-CSF receptor lacking its C-terminus internalizes less efficiently, resulting in the enhanced expression. Since proteins having high contents of proline, glutamic acid, serine, and threonine generally are thought to degrade fast, mutating amino acid sequences to reduce such residues may also be useful to enhance expression.

In the methods of the present invention, cell lines expressing several different chimeric receptors with different extracellular domains can be used if the intracellular domain of the receptors is the same, or if the chimeric receptors induce the same phenotypic change upon ligand binding. The cell lines can induce changes in their phenotypes upon binding to multiple different types of ligands. When the cell lines are cultivated in the presence of a test sample, changes in the cell's phenotypes, for example, cell growth rate, can be detected. In this detection, phenotypic changes in the cultured cell indicate that the test sample is a ligand for at least one of the receptors having multiple extracellular domains. The test samples may be mixed together and it is also possible to simultaneously detect a mixture of natural substances.

The methods of the present invention can be performed by preparing chimeric receptors comprising a common intracellular domain for each of the objective two or more different types of receptors, and preparing cells that separately express each of the chimeric receptors, and mixing these cells when performing the detection. The number of cells mixed is not especially critical as long as the cell number is sufficient to appropriately observe the reactivity to a ligand. When the natural ligand is known, the suitability of the assay system can be evaluated using the natural ligand. The number of cells used is preferably 10 or more per well, more preferably 100 or more per well, even more preferably 1000 or more per well. Since a high concentration of cells decreases the detection sensitivity of cell growth activity, the cell concentration used is preferably $1\times10^7$/mL or less, and more preferably $1\times10^6$/mL or less. Although the assay of the cell growth rate can be usually carried out in 24-well or 96-well plates well known to those skilled in the art, the assay is not restricted by the number of wells of plates used. It is also possible to use plates having 384 wells. In that case, using approximately ¼ of the number of cells used for a 96-well plate is recommended. The detection is possible after one day or more, but preferably 2 to 4 days, more preferably 3 days. The number of cell line types is not critical as long as the phenotypic changes can be detected upon ligand binding. However, the number of types is preferably two or more, more preferably three or more, even more preferably five or more, and most preferably ten or more. The specificity of ligand samples can be determined by using ligand-dependent cells or by detecting their reactivity to individually cultured cells expressing a single chimeric receptor, based on the number of receptors of interest.

The receptor DNA of the present invention can be prepared using methods known in the art. For example, a cDNA library can be constructed from cells expressing a protein of the present invention and hybridization can be conducted using a part of the DNA sequence of interest, which can be found in literature, as a probe. The cDNA library may be prepared, for example, according to the method described by Sambrook J. et al. (Molecular Cloning, Cold Spring Harbor Laboratory Press (1989)), or instead, commercially available DNA libraries may be used. Alternatively, a DNA of the present invention can be obtained by preparing RNA from cells expressing a protein of the present invention, synthesizing cDNA therefrom using a reverse transcriptase, synthesizing oligo-DNA based on a DNA sequence of interest, and amplifying the cDNA encoding a receptor by PCR using the oligo-DNA as primers.

A desired DNA fragment is prepared from the obtained PCR products and linked to a vector DNA. The recombinant vector is used to transform *E. coli* and such, and the desired recombinant vector is prepared from a selected colony. Vector DNA well known to those skilled in the art (pUC19, pBluescript, etc.) can be used for harboring the DNA fragment. *Escherichia coli* strains well known to those skilled in the art (DH5α, JM109, etc.) can be used. The nucleotide sequence of the desired DNA can be verified by conventional methods, such as dideoxynucleotide chain termination (Sambrook, J. et al., Molecular Cloning, Cold Spring Harbor Laboratory Press (1989)). The nucleotide sequence of the desired DNA can be determined by using automated DNA sequencers such as DNA Sequencer PRISM 377 and DNA Sequencer PRISM 310 (Perkin-Elmer), etc.

A DNA of the invention may be designed to have a sequence that is expressed more efficiently by taking into account the frequency of codon usage in the host used for expression (Grantham, R. et al., Nucleic Acids Res. 9:r43-74 (1981)). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG), etc.

To express chimeric receptor molecules, an expression vector, which comprises DNA encoding the chimeric receptor under the control of regulatory sequences such as enhancers/promoters, is constructed. Then, the expression vector is used to simultaneously transform host cells and the chimeric receptor is expressed in the cells. For receptors forming a heterodimer, simultaneous transformation with expression vectors encoding each of the subunits can be done, or an expression vector encoding multiple subunits can be prepared and used for the transformation.

Useful promoters regularly used for expression in mammalian cells can be used. For example, human polypeptide chain elongation factor-1α (HEF-1α) is preferably used. pEFBOS (Mizushima, S. et al. (1990) Nuc. Acid Res. 18, 5322) is an example of expression vectors comprising the HEF-1α promoter. Furthermore, mammalian cell promoters and promoters of viruses, including cytomegalovirus, retrovirus, polyomavirus, adenovirus, simian virus 40 (SV40), and such can be used for the methods of the present invention. For example, the SV40 promoter can be easily utilized by the method of Mulligan et al. (Nature (1990) 277, 108).

To introduce genes into host cells, expression vectors can contain the following selection marker genes; phosphotransferase APH(3') II or I (neo) gene, thymidine kinase gene, *Escherichia coli* xanthine-guanine phosphoribosyl transferase (Ecogpt) gene, dihydrofolate reductase (DHFR) gene, etc.

For introducing genes into hosts, methods well known to those skilled in the art, for example, the calcium phosphate method (Chen, C. et al. (1987) Mol. Cell. Biol. 7, 2745-2752), lipofection (Felgner, PL. et al. (1987) Proc. Natl. Acad. Sci. USA 84, 7413-7417), and electroporation (Potter, H. (1988)

Anal. Biochem. 174, 361-373) can be used. For the methods of the present invention, the electroporation method using a Gene Transfer Equipment (Gene Pulser, Bio-Rad) can be used.

In the methods of the present invention, a further step, wherein biological activity is detected by contacting a test sample with one of the two or more receptors used for the screening, may be included to detect the specificity of a test sample towards a receptor.

Furthermore, the present invention provides kits for the above screening. As components, the kits of the present invention contain (a) two or more kinds of receptors comprising (i) a common signal-transducing domain, and (ii) a domain other than the signal-transducing domain, wherein said domain derives from the same receptor from which the common domain of (i) is derived and/or a different receptor; (b) DNA encoding two or more kinds of receptors comprising (i) a common signal-transducing domain, and (ii) a domain other than the signal-transducing domain, wherein said domain derives from the same receptor from which the common domain of (i) is derived and/or a different receptor; (c) a cell expressing two or more kinds of receptors comprising (i) a common signal-transducing domain, and (ii) a domain other than the signal-transducing domain, wherein said domain derives from the same receptor from which the common domain of (i) is derived and/or a different receptor. By setting up the above screening system using the kit of the present invention, the screening of a ligand can be efficiently done.

It is anticipated that substances (containing ligands) isolated by the screenings of the present invention can be used as pharmaceutical agents for the treatment and prevention of various diseases, depending on their biological activity. For example, it is expected that such a substance can be used as a pharmaceutical agent for the treatment of anemia if it is a ligand for the EPO receptor, for the treatment of neutropenia if it is a ligand for the G-CSF receptor, for the treatment of thrombocytopenia if it is a ligand for the TPO receptor, for the treatment of diabetes if it is a ligand for the insulin receptor, for immunostimulation if it is a ligand for the Flt-3 ligand receptor, for stimulation of wound healing if it is a ligand for the PDGF receptor, for the treatment of viral diseases if it is a ligand for the IFN-α/β receptors, for the treatment of obesity if it is a ligand for the leptin receptor, for the treatment of short statue if it is a ligand for the growth hormone (GH) receptor, for immunosuppression (for example, for the treatment of inflammatory bowel disease and rheumatoid arthritis) if it is a ligand for the interleukin (IL)-10 receptor, for the treatment of short statue if it is a ligand for the insulin-like growth factor (IGF)-I receptor, for the treatment of leukemia if it is a ligand for the leukemia inhibitory factor (LIF) receptor, and for the treatment of obesity (or of amyotrophic lateral sclerosis) if it is a ligand for the ciliary neurotrophic factor (CNTF) receptor.

Such a substance or ligand can be as a pharmaceutical agent for humans and other mammals, such as mice, rats, guinea-pigs, rabbits, chicken, cats, dogs, sheep, pigs, cattle, monkeys, baboons, and chimpanzees. Specifically, it can either itself be directly administered to subjects or it can be formulated using known pharmaceutical preparation methods for administration. For example, according to the need, the substances or ligands can be taken orally, as sugar coated tablets, capsules, elixirs, and microcapsules; or non-orally, in the form of injections of sterile solutions or suspensions with water or any other pharmaceutically acceptable liquid. For example, the substances or ligands can be formulated by mixing appropriately with pharmacologically acceptable carriers or medium, such as, sterilized water, physiological saline, plant-oil, emulsifiers, suspending agents, surfactants, stabilizers, flavoring agents, excipients, vehicles, preservatives, and binders, in a unit dose form required for generally accepted drug implementation. The amount of active ingredient in these preparations makes a suitable dosage within the indicated range acquirable.

Examples of additives that can be mixed for tablets and capsules are, binders such as gelatin, corn starch, tragacanth gum, and arabic gum; excipients such as crystalline cellulose; swelling agents such as corn starch, gelatin, and alginic acid; lubricants such as magnesium stearate; sweeteners such as sucrose, lactose, or saccharin; flavoring agents such as peppermint, Gaultheria adenothrix oil, and cherry. When the unit dosage form is a capsule, a liquid carrier, such as oil, can also be included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as a solubilizer or may be formulated with a buffer such as phosphate buffer and sodium acetate buffer, a pain-killer such as procaine hydrochloride, a stabilizer such as benzyl alcohol, phenol, or an anti-oxidant. The prepared injection is generally filled into a suitable ampule.

Methods well known to one skilled in the art may be used to administer a pharmaceutical compound to patients, for example as intraarterial, intravenous, subcutaneous injections and also as intranasal, transbronchial, intramuscular, percutaneous, or oral administrations. The dosage varies according to the body-weight and age of a patient, and the administration method; however, one skilled in the art can suitably select the dosage.

Although varying according to the symptoms and such, the dose may be generally in the range of about 0.1 mg to about 500 mg, preferably about 1.0 mg to about 100 mg, and more preferably about 1.0 mg to about 20 mg per day for adults (body weight: 60 kg) in the case of an oral administration.

Although varying according to the subject, target organ, symptoms, and method of administration, a single dose of a compound for parenteral administration is advantageous, for example, when administered intravenously to normal adults (60 kg body weight) in the form of injection, in the range of about 0.01 mg to about 30 mg, preferably about 0.1 mg to about 20 mg, and more preferably about 0.1 mg to about 10 mg per day. Doses converted to 60 kg body weight or per body surface area can be administered to other animals.

An evident growth reaction against human PDGF-BB was observed at concentrations of 0.5 ng/mL or more.

Figure 18:
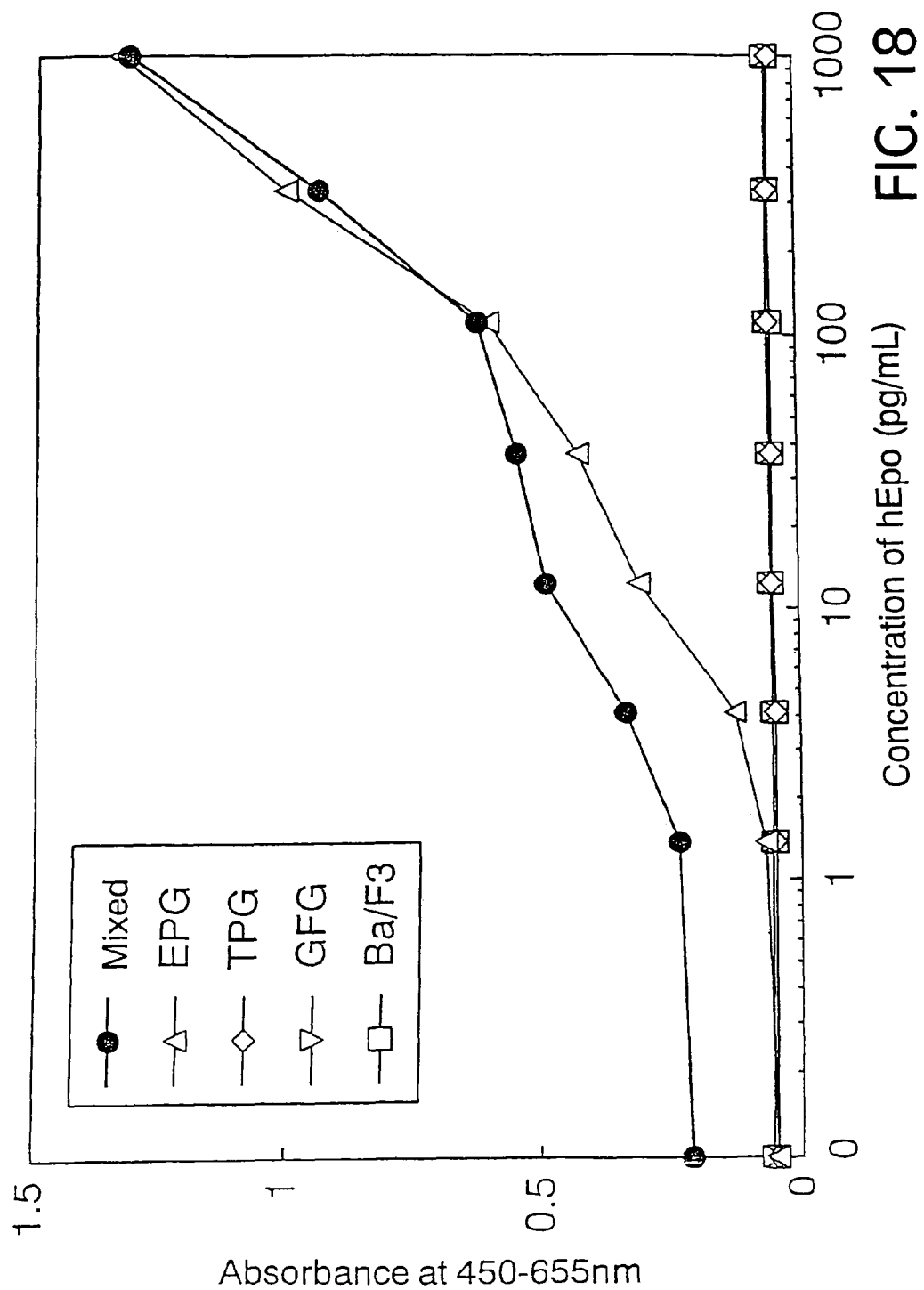

FIG. 18 depicts responses of cells to human EPO in individual and mixed cell culture systems. Open symbols indicate the responses of the individually cultured established cell lines ($4\times10^3$ cells/well), and closed circles those of the mixed culture of the four cell lines (each cell line at $4\times10^3$ cells/well, $16\times10^3$ cells/well in total). In comparison to the individual cultures (open upward triangle), a slight enhancement in the growth activity was observed for the mixed culture (closed circle) in the absence of human EPO. However, the response to human EPO was observed to be similar between those at the concentration 1 to 10 pg/mL, where the response was observed to start, and at maximum stimulation.

Figure 19:
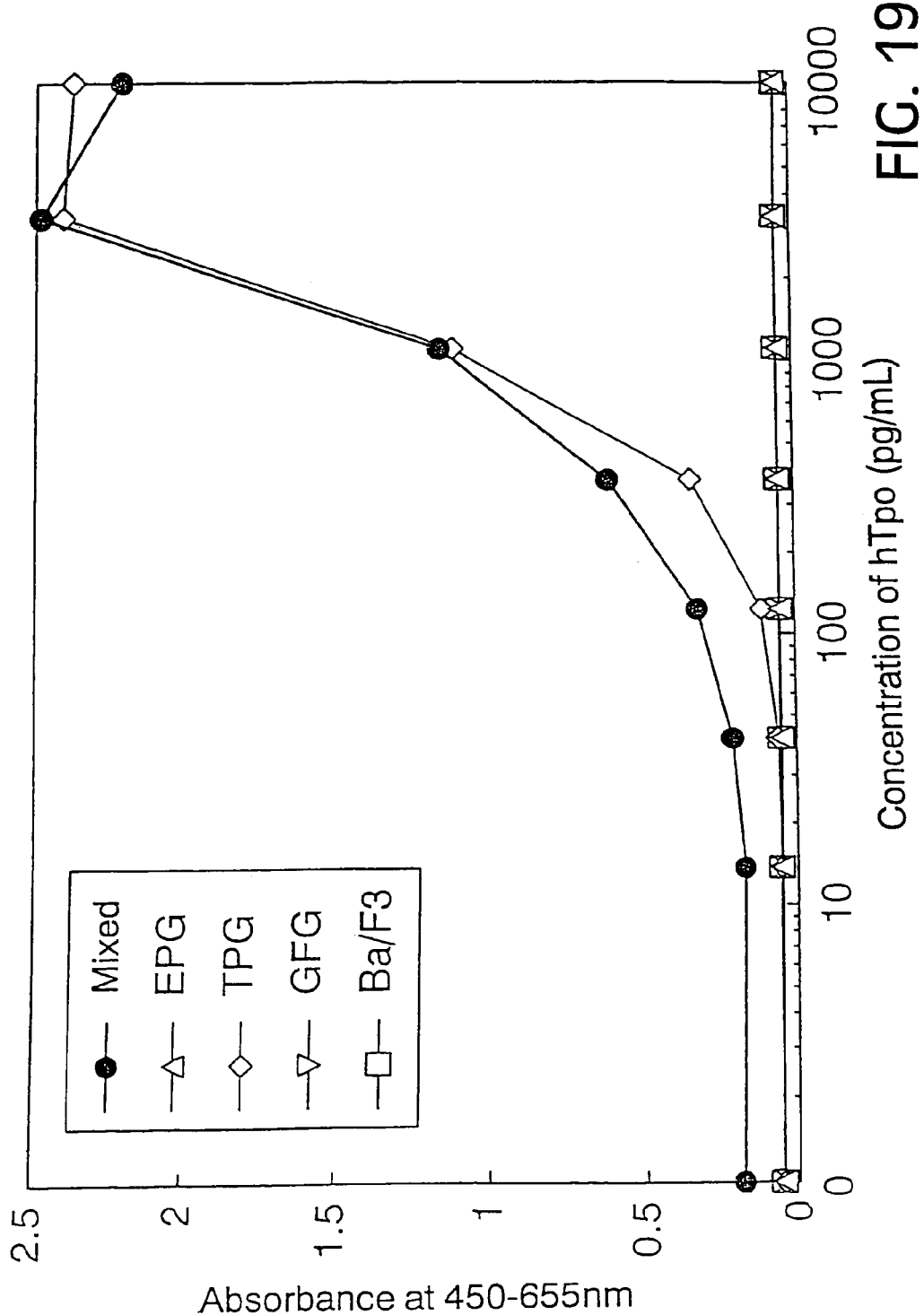

FIG. 19 depicts the responses of cells to human TPO in individual and mixed culture systems. Open symbols indicate the responses of the individually cultured established cell lines ($4\times10^3$ cells/well), and closed circles those of the mixed culture of the four cell lines (each cell line at $4\times10^3$ cells/well, $16\times10^3$ cells/well in total). In comparison to the individual cultures (open diamond), a slight enhancement in the growth activity was observed for the mixed culture (closed circle) in the absence of human TPO. However, the response to human TPO was observed to be similar between those at the concentration 100 to 300 pg/mL, where the response was observed to start, and at maximum stimulation.

Figure 20:
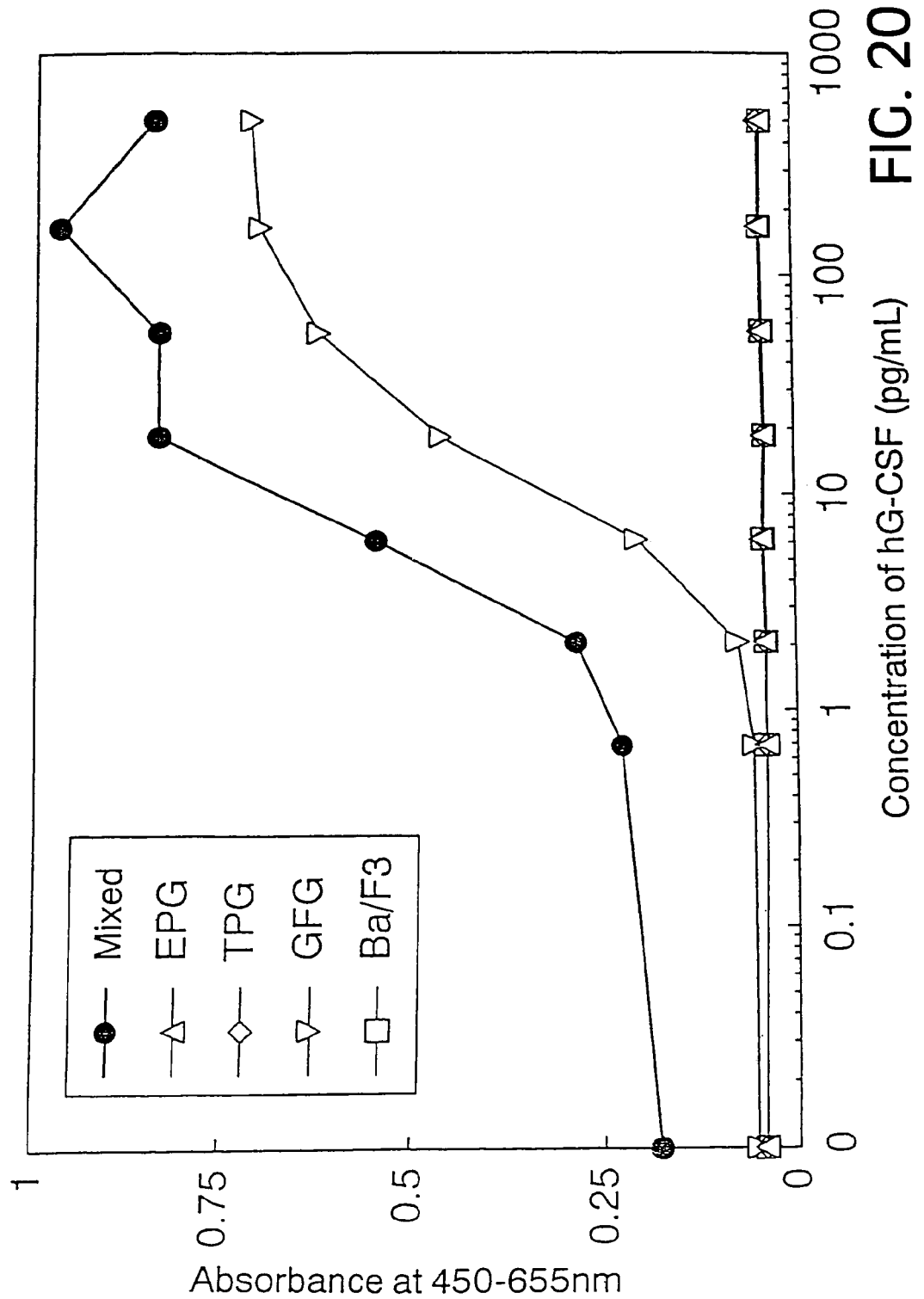

FIG. 20 depicts the responses of cells to human G-CSF in individual and mixed culture systems. Open symbols indicate the responses of the individually cultured established cell lines ($4\times10^3$ cells/well), and closed circles those of the mixed culture of the four cell lines (each cell line at $4\times10^3$ cells/well, $16\times10^3$ cells/well in total). In comparison to the individual culture (open downward triangle), a slight enhancement in the growth activity was observed for the mixed culture (closed circle) in the absence of human G-CSF. However, the response to human G-CSF was observed to be similar between those at the concentration 2 to 5 pg/mL, where the response was observed to start, and at maximum stimulation.

BEST MODE FOR CARRYING OUT THE INVENTION

The present invention will be described in more detail below by way of Examples, but should not be construed as being limited to these Examples.

EXAMPLE 1

Establishment of Cell Lines Expressing Chimeric Receptors (1-1) Construction of Mammalian Cell Expression Plasmid Vectors, PCOS-G, pCOS2, and pCV Mammalian cell plasmid expression vector pCOS-G was constructed by replacing the polyadenylation signal of pCOS1 (see International Publication No. WO98/13388, "Antibody against human parathormone related peptides") with that of the human G-CSF gene. The polyadenylation signal of human G-CSF gene was obtained by digesting pEF-BOS (Mizushima S. et al. (1990) Nuc. Acid Res. 18, 5322) with Xho I and Pvu II. The polyadenylation signal fragment was replaced into the Xho I/Aor51H I fragment of pCOS1, and the resulting construct was dubbed PCOS-G.

Mammalian cell plasmid expression vector pCOS2 was constructed by replacing the BamHI/Aor51H I fragment of pCOS1 with the BamHI/Aor51HI fragment of pEGFP-N1 (CLONTECH).

Mammalian cell plasmid expression vector pCV was constructed by replacing the polyadenylation signal of pCOS1 with that of the human G-CSF gene. The polyadenylation signal of human G-CSF gene was obtained by digesting pEF-BOS with EcoRI and Xba I. The 3' end of the fragment was blunted, and a BamHI site was attached to the 5' end of the fragment. The resulting fragment was replaced as the poly (A) addition signal into the BamHI/Aor51H I site of pCOS1, and was used as pCV.

(1-2) Erythropoietin (Hereinafter, Referred to as EPO) Receptor

A chimeric receptor cDNA was constructed by linking cDNA fragments encoding the extracellular domain (from the 1st to the 249th amino acid residues; Jones, SS. et al. (1990) Blood, 76, 31-35) of human EPO receptor, and the transmembrane and intracellular domains (from the 602nd to the 813th amino acid residues; Fukunaga, R. et al. (1990) Cell 61, 341-350) of mouse G-CSF receptor. The cDNA was inserted downstream of the EF1α promoter of the mammalian expression vector pCOS-G to construct chimeric receptor-expression vector EG/pCOS-G. EG/pCOS-G was linearized using Pvu I (Takara Shuzo), extracted with phenol and chloroform, and purified by ethanol precipitation.

The linearized expression vector was introduced into mouse FDC-P1 cells (ATCC No. CRL-12103) using an electroporation apparatus (Gene Pulser: Bio Rad). The FDC-P1 cells were washed twice with Dulbecco's PBS (hereinafter referred to as PBS), and were suspended in PBS to give a cell density of about $1 \times 10^7$ cells/mL. 10 μg of the linearized expression vector DNA was added to 0.8 mL of the suspension, transferred into a cuvette for electroporation (Bio Rad), and pulsed with a capacitance of 250 μF at 0.35 kV.

After standing still at room temperature for about 10 min, the cells treated by electroporation were suspended in Media A that was supplemented with 1 ng/mL human EPO (prepared from genetic recombinant CHO cells), and then were seeded on a 96-well microtiter plate (flat bottom, Falcon) at 100 μL/well. After culturing in a $CO_2$ incubator ($CO_2$ concentration, 5%) for about six hours, 100 μL/well of Media A supplemented with 1 ng/mL EPO and 1 mg/mL GENETICIN (GIBCO) was added to the plate, and was cultured in a $CO_2$ incubator ($CO_2$ concentration, 5%). RPMI1640 (GIBCO) supplemented with 10% fetal bovine serum (GIBCO), 100 U/mL penicillin, and 0.1 mg/mL streptomycin (GIBCO) was used as Media A. About one week after the start of the culture, cells were observed under a microscope, and cells were collected from wells with a single colony. The collected cells were subcultured in Media A containing 1 ng/mL human EPO. The titer of human EPO used in this Example was 270,000 IU/mg.

Figure 1:
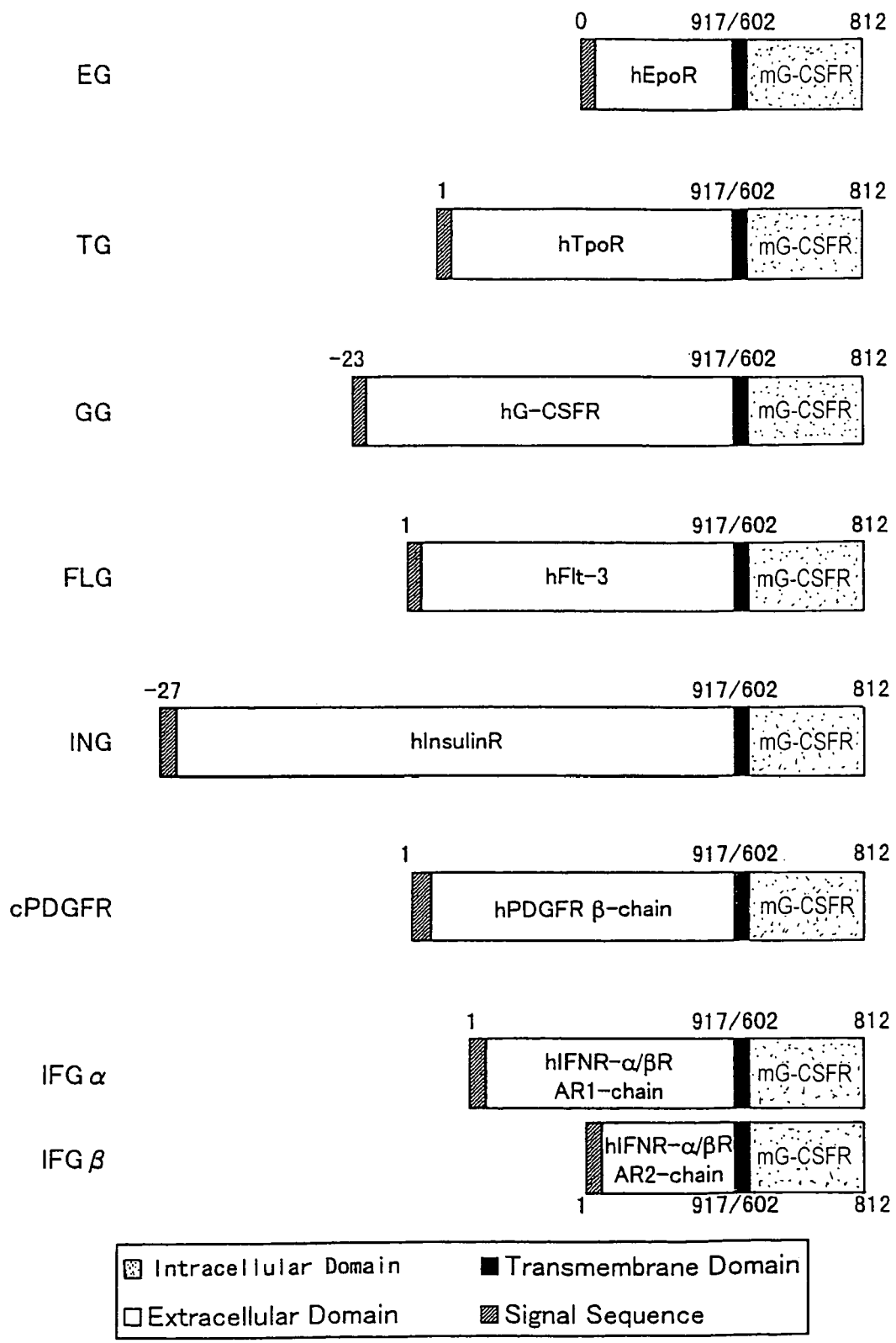
FIG. 1 depicts the amino acid sequences of the used chimeric receptors. The extracellular domains were derived from various human receptors, and the intracellular domains from mouse G-CSF receptor (from the 602nd to the 812th amino acid residues of mouse G-CSF receptor).
Figure 2:
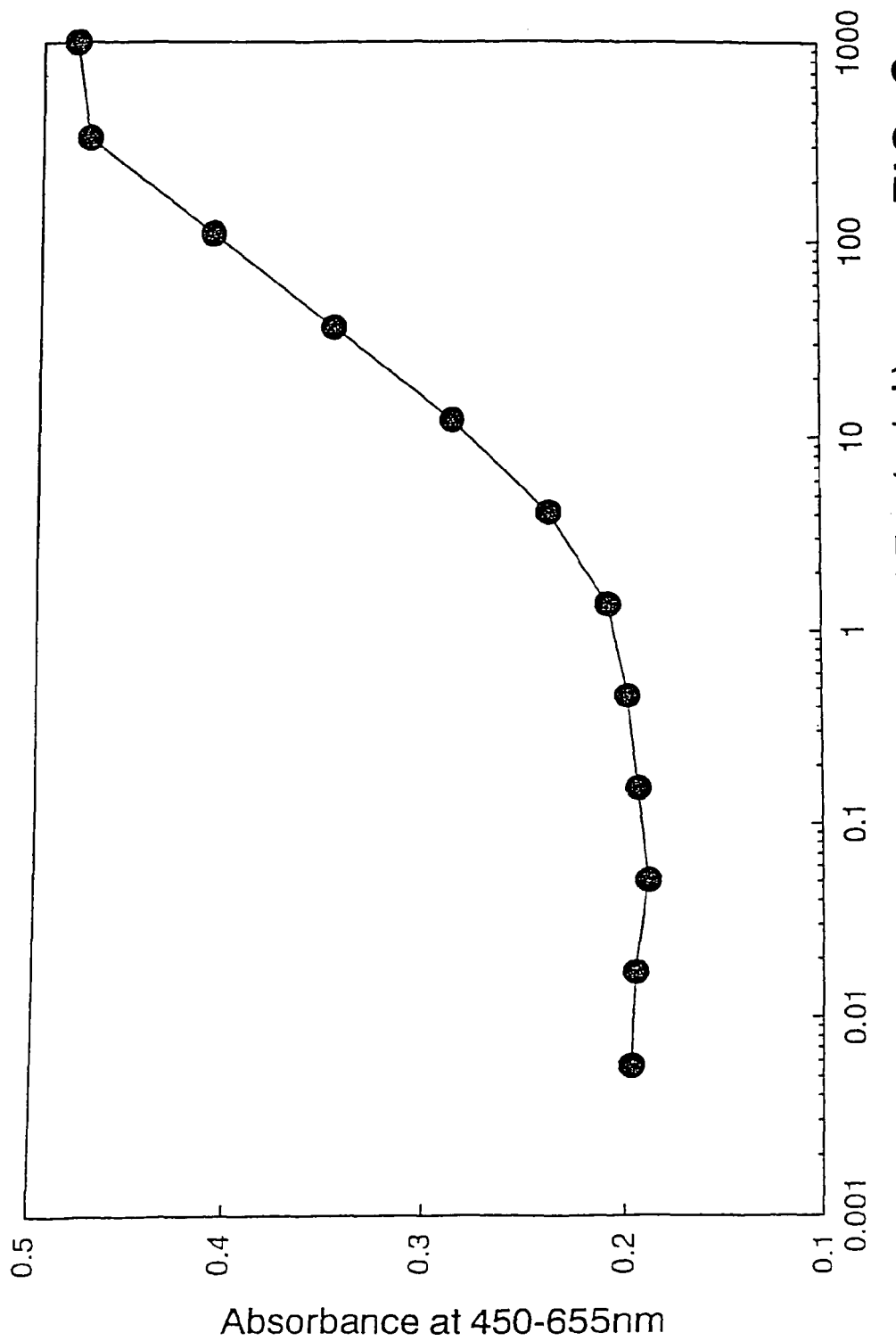
FIG. 2 depicts the response of the chimeric EPO receptor-expressing FDC-P1 cell line F#14 against human EPO. An evident growth reaction against human EPO was observed at concentrations of 10 pg/mL or more.

The cells were washed twice with Media A, and then suspended in Media A to give a cell density of $2 \times 10^5$ cells/mL. 50 μl/well of the cell suspension and 50 μl/well of human EPO, appropriately diluted with Media A, were dispensed into wells of a 96-well microtiter plate (flat bottom, Falcon), and were cultured for 24 hours in a $CO_2$ incubator ($CO_2$ concentration, 5%). After the culture, 10 μl/well WST-8 reagent (Cell Counting Kit-8; DOJINDO LABORATORIES) was added, and the plate was incubated for five hours in a $CO_2$ incubator ($CO_2$ concentration, 5%). Then, absorbance at a measurement wavelength of 450 nm and a control wavelength of 655 nm was measured using microplate reader (Model 3550, Bio Rad). Based on the cell growth activity determined by the number of viable cells as the index by plotting the absorbance measured after the five-hour incubation on the vertical axis and the concentrations of human EPO on the horizontal axis, cell line F#14 that had a high sensitivity to human EPO was selected (FIG. 2).

The linearized expression gene vector was introduced into mouse Ba/F3 cells (purchased from RIKEN; Cell No.: RCB0805) using an electroporation apparatus (Gene Pulser, BIO Rad). The Ba/F3 cells were washed twice with Dulbecco's PBS (hereinafter referred to as PBS), and then were suspended in PBS to give a cell density of about $1 \times 10^7$ cells/mL. 10 μg of the linearized expression vector DNA was added to 0.8 mL of this suspension, transferred into a cuvette (Bio Rad) for electroporation, and pulsed with a capacitance of 960 μF at 0.33 kV.

Figure 3:
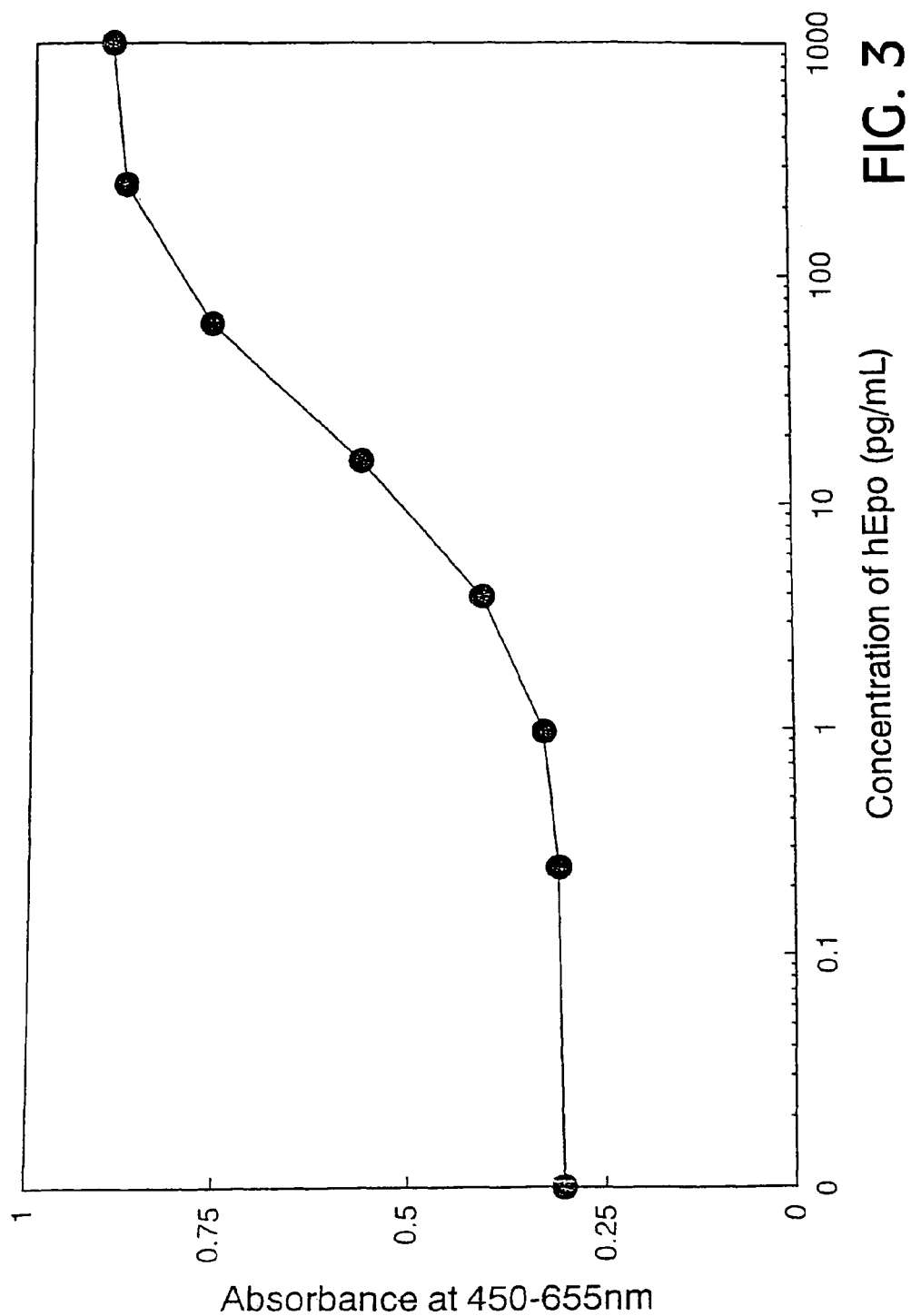
FIG. 3 depicts the response of the chimeric EPO receptor-expressing Ba/F3 cell line EPG against human EPO. An evident growth reaction against human EPO was observed at concentrations of 10 pg/mL or more.

After leaving standing for about 10 min at room temperature, the cells treated by electroporation were suspended in Media A containing 1 ng/mL human EPO, and then were seeded on a 96-well microtiter plate (flat bottom, Falcon) at 100 μl/well. After culturing the cells for about five hours in a $CO_2$ incubator ($CO_2$ concentration, 5%), 100 μL/well Media A that contained 1 ng/mL human EPO and 1 mg/mL GENETICIN (GIBCO) was added, and the cells were cultured in a $CO_2$ incubator ($CO_2$ concentration, 5%). RPMI1640 (GIBCO) supplemented with 10% fetal bovine serum (GIBCO), 100 U/mL penicillin, and 0.1 mg/mL streptomycin (GIBCO) was used as Media A. About one week after the start of the cultivation, cells were observed under a microscope, cells were collected from wells with a single colony, and were subcultured in Media A containing 1 ng/mL human EPO. The cells were washed twice with Media A, and were suspended in Media A to give a cell density of $2 \times 10^5$ cells/mL. 50 μl/well of the cell suspension and 50 μl/well of human EPO appropriately diluted with Media A were dispensed into the wells of a 96-well microtiter plate (flat bottom, Falcon), and were cultured for 24 hours in a $CO_2$ incubator ($CO_2$ concentration, 5%). After the culture, 10 μl/well WST-8 reagent (Cell Counting Kit-8; DOJINDO LABORATORIES) was added, and the plate was incubated for five hours in a $CO_2$ incubator ($CO_2$ concentration, 5%). After the incubation, absorbance at a measurement wavelength of 450 nm and a control wavelength of 655 nm was measured using microplate reader (Model 3550, Bio Rad). Based on the cell growth activity determined by the number of viable cells as an index by plotting the absorbance measured after the five-hour incubation on the vertical axis and the concentrations of human EPO on the horizontal axis, cell line B#20 that had a high sensitivity to human EPO was selected, and was used as chimeric EPO receptor-expressing cell line EPG (FIG. 3). Similar growth responses to human EPO were observed by using FDC-P1 and Ba/F3 as host cells.

(1-3) Thrombopoietin (Hereinafter Referred to as TPO) Receptor

A chimeric receptor cDNA was constructed by linking cDNA fragments encoding the extracellular domain (from the 1st to the 491st amino acid residues; Vigon, I. et al. (1992) Proc. Natl. Acad. Sci. USA 89, 5640-5644) of human TPO receptor, and the transmembrane and intracellular domains (from the 602nd to the 813th amino acid residues; Fukunaga, R. et al. (1990) Cell 61, 341-350) of mouse G-CSF receptor. The cDNA was inserted downstream of the EF1α promoter of the mammalian expression vector pCOS-G to construct chimeric receptor-expression vector TG/pCOS-G. TG/pCOS-G was linearized with Pvu I (Takara Shuzo), extracted with phenol and chloroform, and purified by ethanol precipitation.

The linearized expression gene vector was introduced into mouse Ba/F3 cells (purchased from RIKEN; Cell No.: RCB0805) using an electroporation apparatus (Gene Pulser: Bio Rad) The Ba/F3 cells were washed twice with Dulbecco's PBS (hereinafter referred to as PBS), and then were suspended in PBS to give a cell density of about $1 \times 10^7$ cells/mL. 10 μg of the linearized expression vector DNA was added to 0.8 mL of this suspension, transferred into a cuvette (Bio Rad) for electroporation, and was pulsed with a capacitance of 960 μF at 0.33 kV.

After leaving standing for about 10 min at room temperature, the cells treated by electroporation were suspended in Media A, and were seeded on a 96-well microtiter plate (flat bottom, Falcon) at 100 µL/well. 100 µL/well Media A that contained 2 ng/mL human TPO (R&D Systems) and 1 mg/mL GENETICIN (GIBCO) was added, and the cells were cultured in a $CO_2$ incubator ($CO_2$ concentration, 5%). RPMI1640 (GIBCO) supplemented with 10% fetal bovine serum (GIBCO), 100 U/mL penicillin, and 0.1 mg/mL streptomycin (GIBCO) was used as Media A. About one week after the start of culture, the cells were observed under a microscope, cells were collected from wells with a single colony and were subcultured in Media A containing 1 ng/mL human TPO.

Figure 4:
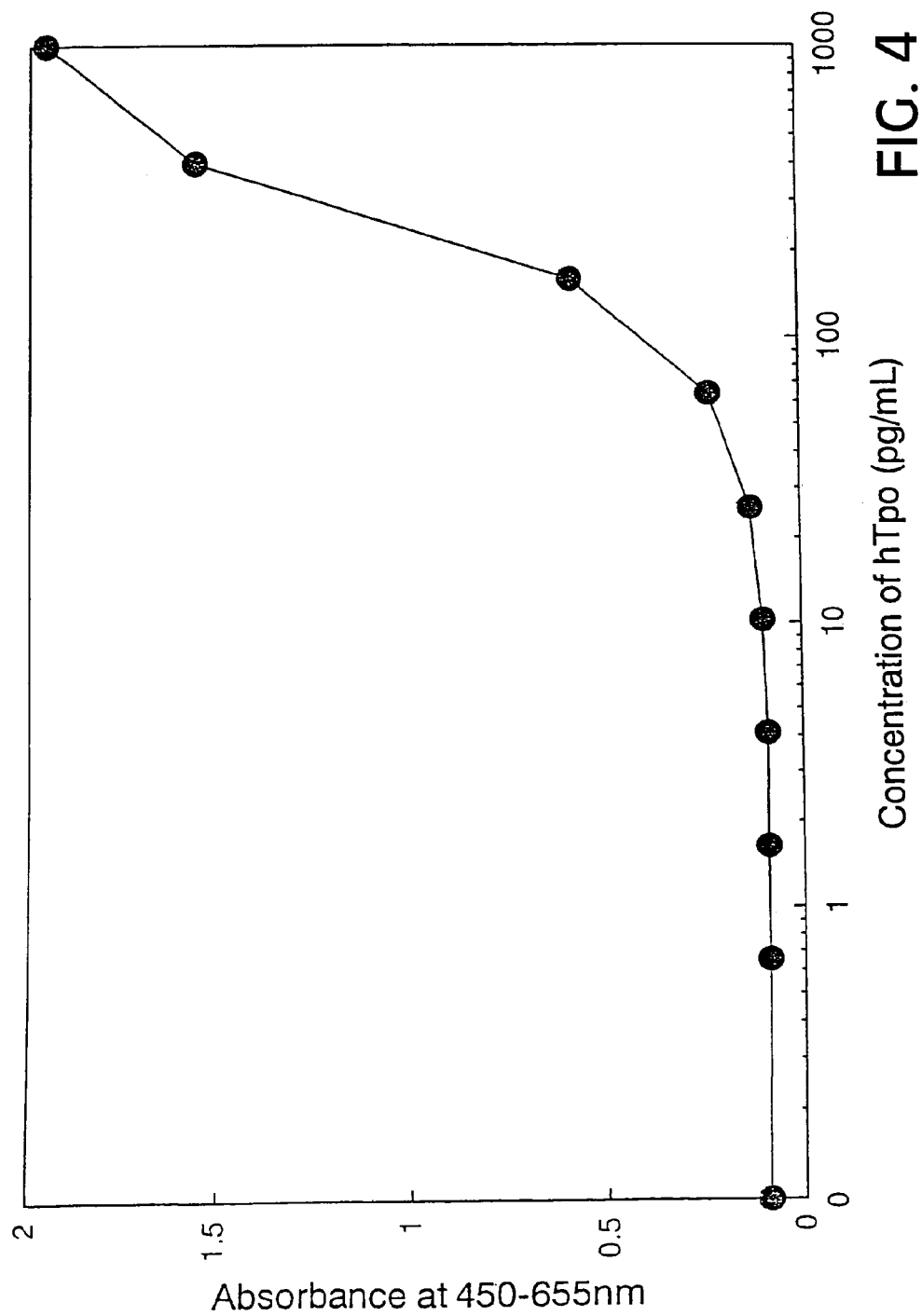
FIG. 4 depicts the response of the chimeric TPO receptor-expressing Ba/F3 cell line TPG against human TPO. An evident growth reaction against human TPO was observed at concentrations of 100 pg/mL or more.

The cells were washed twice with Media A, and were suspended in Media A to give a cell density of $5 \times 10^4$ cells/mL. 50 µl/well cell suspension and 50 µl/well of human TPO (R&D Systems) appropriately diluted with Media A were dispensed into the wells of a 96-well microtiter plate (flat bottom, Falcon), and were cultured for 72 hours in a $CO_2$ incubator ($CO_2$ concentration, 5%). After the culture, 10 µl/well WST-8 reagent (Cell Count Reagent SF; Nacalai Tesque) was added, and the plate was incubated for two hours in a $CO_2$ incubator ($CO_2$ concentration, 5%). The absorbance at a measurement wavelength of 450 nm and a control wavelength of 655 nm after the 2 hours incubation was measured using microplate reader (Model 3550, Bio Rad). Based on the cell growth activity determined by the number of viable cells as an index by plotting the absorbance measured after the two-hour incubation on the vertical axis and the concentrations of human TPO on the horizontal axis, cell line TPG#219 that had a high sensitivity to human TPO was selected and was used as chimeric TPO receptor-expressing cell line TPG (FIG. 4).

(1-4) Granulocyte-Colony Stimulating Factor (Hereinafter Referred to as G-CSF) Receptor A chimeric receptor cDNA was constructed by linking cDNA fragments encoding the extracellular domain (from the −23rd to the 604th amino acid residues; Fukunaga, R. et al. (1990) Proc. Natl. Acad. Sci. USA 87, 8702-8706) of human G-CSF receptor, and the transmembrane and intracellular domains (from the 602nd to the 813th amino acid residues; Fukunaga, R. et al. (1990) Cell 61, 341-350) of mouse G-CSF receptor. The cDNA was inserted downstream of the HEF1α promoter of the mammalian expression vector pCOS-G to construct chimeric receptor-expression vector GG/pCOS-G. GG/pCOS-G was linearized with Pvu I (Takara Shuzo), extracted with phenol and chloroform, and purified by ethanol precipitation.

The linearized expression gene vector was introduced into mouse Ba/F3 cells using an electroporation apparatus (Gene Pulser: Bio Rad). The Ba/F3 cells were washed twice with Dulbecco's PBS (hereinafter referred to as PBS), and then were suspended in PBS to give a cell density of about $1 \times 10^7$ cells/mL. 10 µg of linearized expression vector DNA was added to 0.8 mL of this suspension, transferred into a cuvette (Bio Rad) for electroporation, and was pulsed with a capacitance of 960 µF at 0.33 kV.

After leaving standing for about 10 min at room temperature, the cells treated by electroporation were suspended in Media A, and were seeded on a 96-well microtiter plate (flat bottom, Falcon) at 100 µL/well. 100 µL/well Media A containing 2 ng/mL human G-CSF was added, and the cells were cultured in a $CO_2$ incubator ($CO_2$ concentration, 5%). RPMI1640 (GIBCO) supplemented with 10% fetal bovine serum (Hyclone) 100 U/mL penicillin, and 0.1 mg/mL streptomycin (GIBCO) was used as Media A. After about one week from the start of the culture, the cells were observed under a microscope, cells were collected from wells with a single colony and were subcultured in Media A containing 10 ng/mL human G-CSF. The human G-CSF used in this Example was prepared from recombinant CHO cells, and the titer of human G-CSF was $1.2 \times 10^8$ IU/mg.

Figure 5:
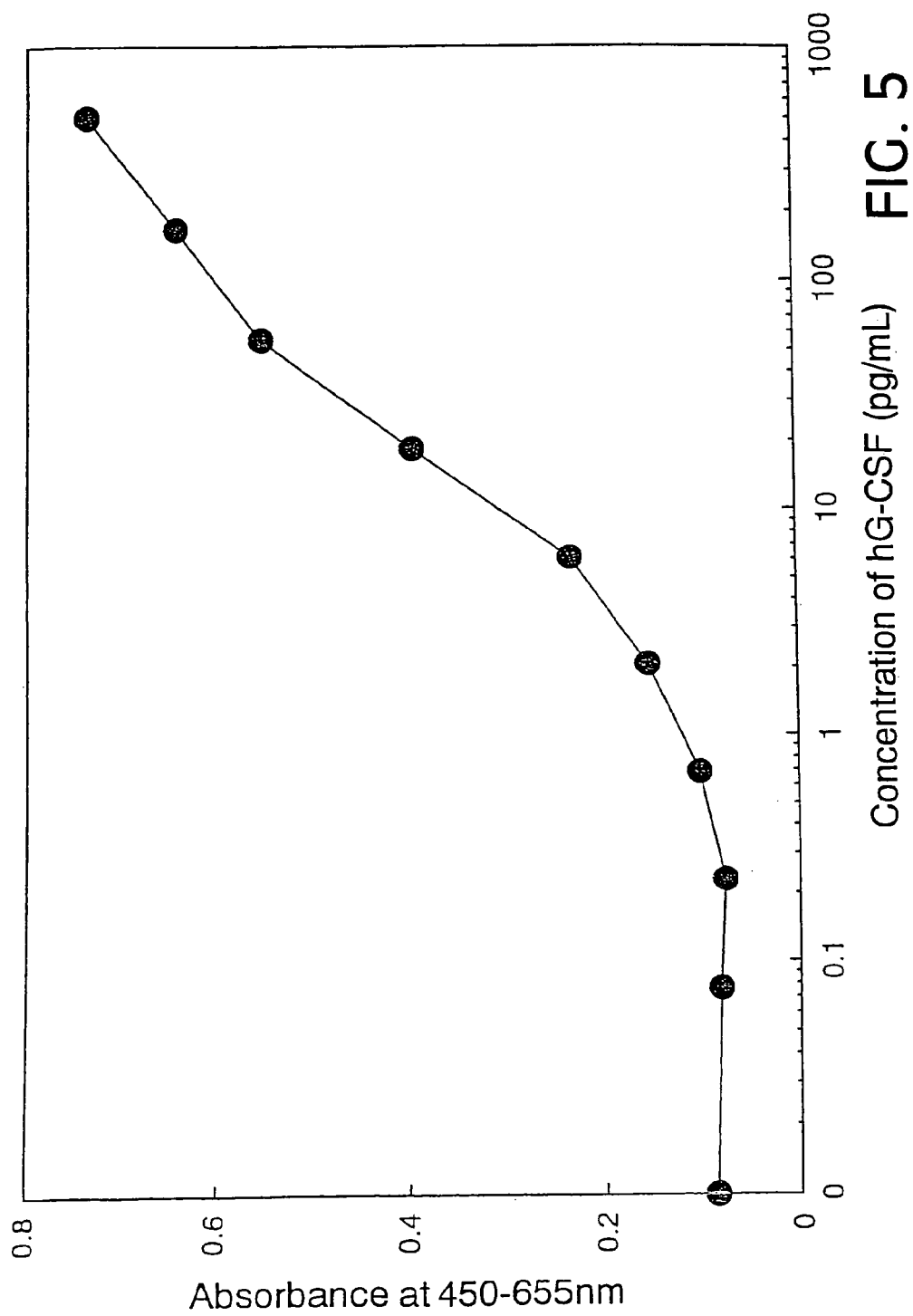
FIG. 5 depicts the response of the chimeric G-CSF receptor-expressing Ba/F3 cell line GFG against human G-CSF. An evident growth reaction against human G-CSF was observed at concentrations of 10 pg/mL or more.

The cells were washed twice with Media A, and were suspended in Media A to give a cell density of $5 \times 10^4$ cells/mL. 50 µl/well cell suspension and 50 µl/well of human G-CSF (prepared from recombinant CHO cells) appropriately diluted in Media A were dispensed into wells of a 96-well microtiter plate (flat bottom, Falcon), and were cultured for 70 hours in a $CO_2$ incubator ($CO_2$ concentration, 5%). After the culture, 10 µl/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of changes in absorbance after the two-hour incubation on the vertical axis and the concentrations of human G-CSF on the horizontal axis, cell line GFG#342 that had a high sensitivity to human G-CSF was selected and used as chimeric G-CSF receptor-expressing cell line GFG (FIG. 5).

(1-5) Flt-3/Flk-2 Ligand (Hereinafter Referred to as Flt-3 Ligand) Receptor

A chimeric receptor cDNA was constructed by linking cDNA fragments encoding the extracellular domain (from the 1st to the 541st amino acid residues; Small, D. et al. (1994) Proc. Natl. Acad. Sci. USA. 91, 459-463) of human Flt-3, and the transmembrane and intracellular domains (from the 602nd to the 813th amino acid residues; Fukunaga, R. et al. (1990) Cell 61, 341-350) of mouse G-CSF receptor. The cDNA was inserted downstream of the EF1α promoter of the mammalian expression vector pCOS2 to construct chimeric receptor-expression vector FLG/pCOS2. The FLG/pCOS2 was linearized with Hpa I (Takara Shuzo), extracted with phenol and chloroform, and purified by ethanol precipitation.

The linearized expression gene vector was introduced into mouse Ba/F3 cells using an electroporation apparatus (Gene Pulser: Bio Rad). The Ba/F3⁻ cells were washed twice with Dulbecco's PBS (hereinafter referred to as PBS), and then were suspended in PBS to give a cell density of about $1 \times 10^7$ cells/mL. 10 µg of the linearized expression vector DNA was added to 0.8 mL of this suspension, transferred into a cuvette (Bio Rad) for electroporation, and pulsed with a capacitance of 960 µF at 0.33 kV.

After leaving standing for about 10 min at room temperature, the cells treated by electroporation were suspended in Media A, and were seeded on a 96-well microtiter plate (flat bottom, Falcon) at 100 µL/well. 100 µL/well Media A that contained 10 ng/mL human Flt-3 ligand (Genzyme) was added, and the cells were cultured in a $CO_2$ incubator ($CO_2$ concentration, 5%). RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells with a single colony and subcultured in Media A containing 5 ng/mL human Flt-3 ligand.

Figure 6:
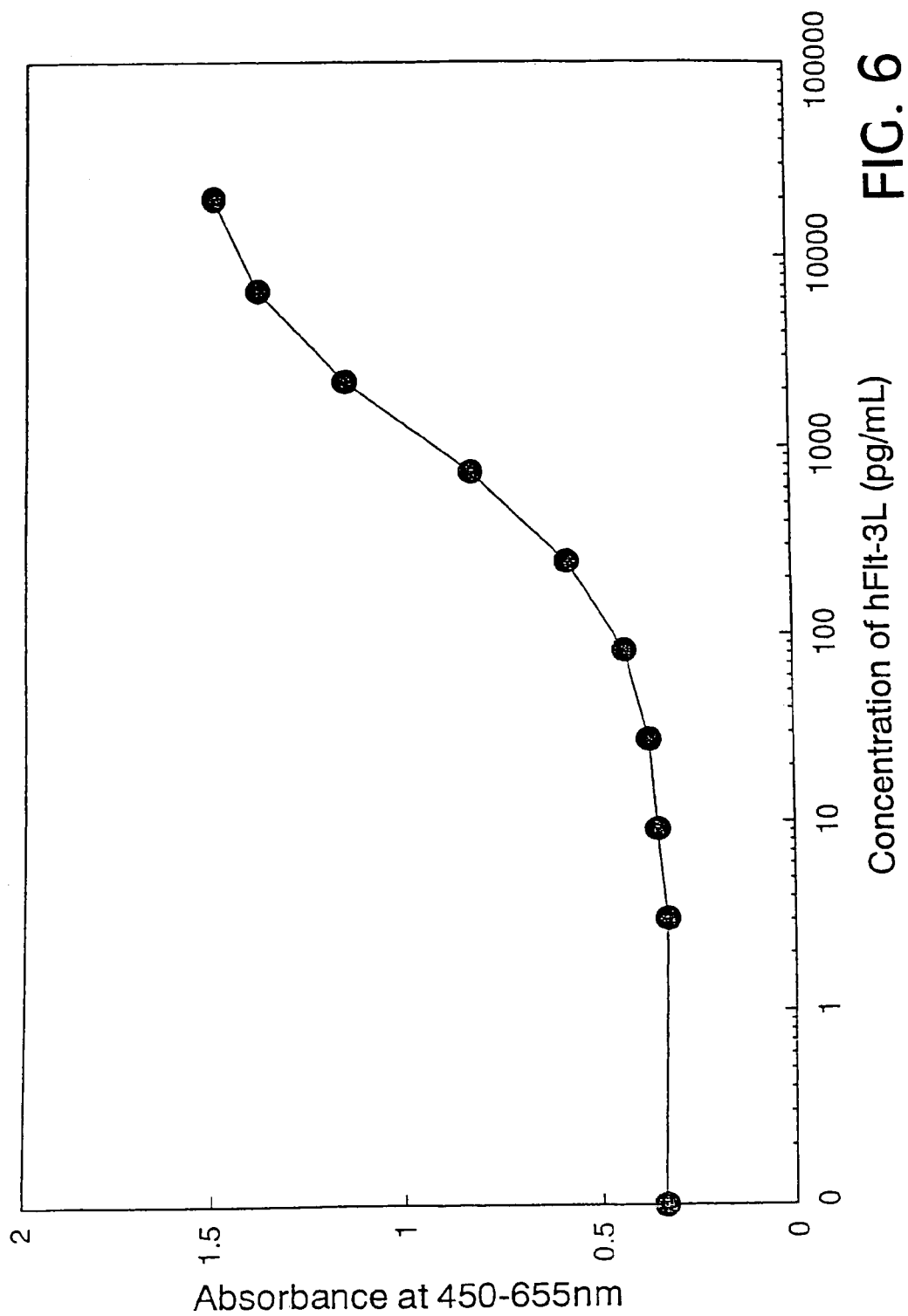
FIG. 6 depicts the response of the chimeric Flt-3 receptor-expressing Ba/F3 cell line FLG against human Flt-3 ligand. An evident growth reaction against human Flt-3 ligand was observed at concentrations of 300 pg/mL or more.

The cells were washed twice with Media A, and were suspended in Media A to give a cell density of $5 \times 10^4$ cells/ mL. 50 µl/well cell suspension and 50 µl/well of human Flt-3 ligand appropriately diluted in Media A were dispensed into wells of a 96-well microtiter plate (flat bottom, Falcon), and were cultured for 74 hours in a $CO_2$ incubator ($CO_2$ concentration, 5%). After the culture, 10 µl/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%; humidity, 99.9%), and post-reaction absorbance was measured as above. Based on the cell growth activity determined by the number of viable cells by plotting the amount of change in absorbance after the two-hour incubation on the vertical axis and the concentrations of human Flt-3 ligand on the horizontal axis, cell line FLG#102 that had a high sensitivity to human Flt-3 ligand was selected and used as chimeric Flt-3 ligand receptor-expressing cell line FLG (FIG. 6).

(1-6) Insulin Receptor

A chimeric receptor cDNA was constructed by linking cDNA fragments encoding the extracellular domain (from the −27th to the 917th amino acid residues; Ullrich, A. et al. (1985) Nature 313, 756-761) of human insulin receptor, and the transmembrane and intracellular domains (from the 602nd to the 813th amino acid residues,; Fukunaga, R. et al. (1990) Cell 61, 341-350) of mouse G-CSF receptor. The cDNA was inserted downstream of the HEF1α promoter of the mammalian expression vector pCV to construct chimeric receptor-expression vector ING/pCv. ING/pCV was linearized with Pvu I (Takara Shuzo) extracted with phenol and chloroform, and purified by ethanol precipitation.

The linearized expression gene vector was introduced into mouse Ba/F3 cells using an electroporation apparatus (Gene Pulser: Bio Rad). The Ba/F3 cells were washed twice with Dulbecco's PBS (hereinafter referred to as PBS), and then were suspended in PBS to give a cell density of about $1 \times 10^7$ cells/mL. 10 µg of the linearized expression, vector DNA was added to 0.8 mL of this suspension, transferred into a cuvette (Bio Rad) for electroporation, and pulsed with a capacitance of 960 µF at 0.33 kV.

After leaving standing for about 10 min at room temperature, the cells treated by electroporation were suspended in Media A, and were seeded on a 96-well microtiter plate (flat,bottom, Falcon) at 100 µL/well. 100 µL/well Media A containing 10 µg/mL human insulin (SIGMA) was added, and the cells were cultured in a $CO_2$ incubator ($CO_2$ concentration, 5%). RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells with a single colony and subcultured in Media A containing 10 µg/mL human insulin.

Figure 7:
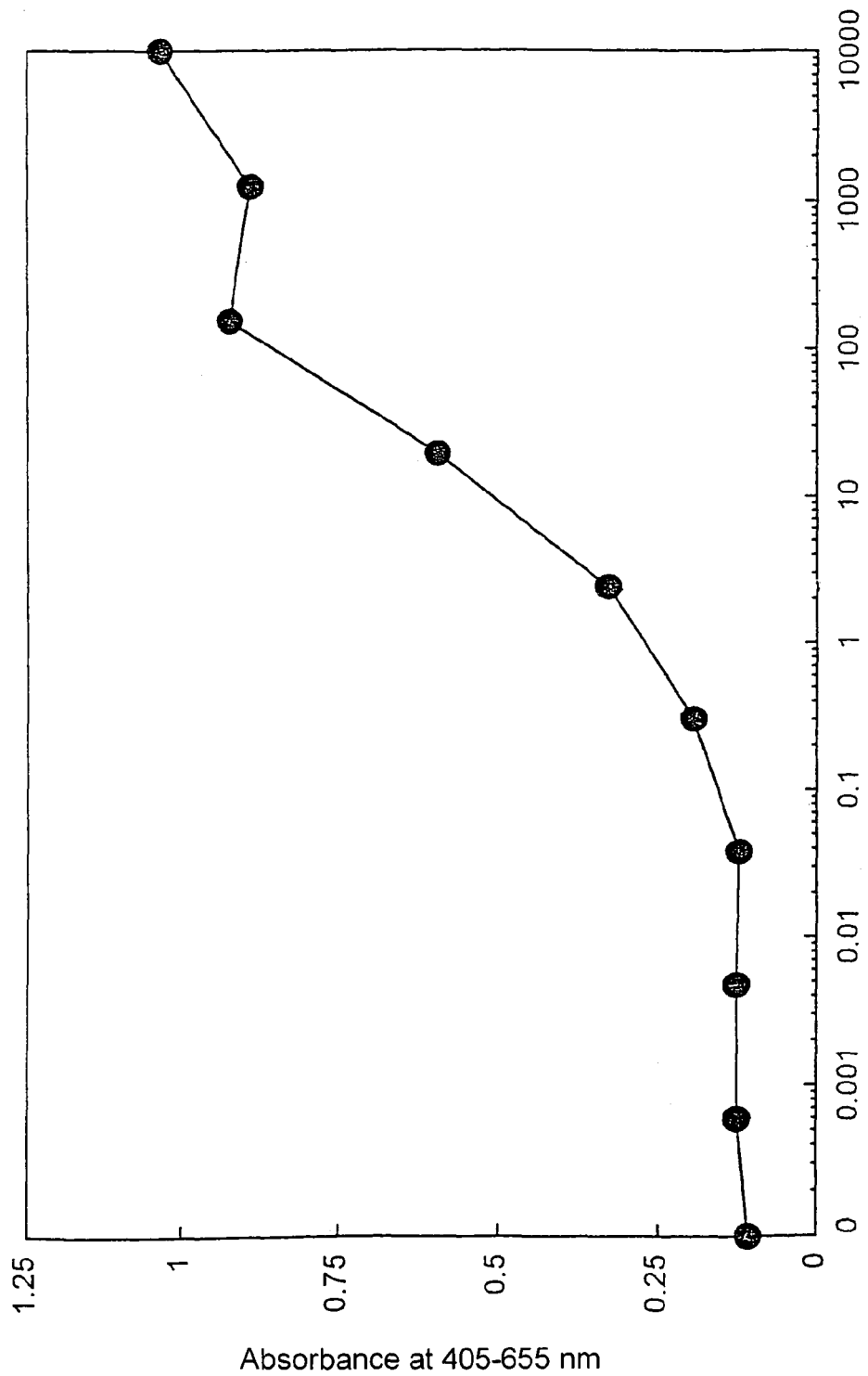
FIG. 7 depicts the response of the chimeric insulin receptor-expressing cell line ING against human insulin.

The cells were washed twice with media without human insulin (hereinafter referred to as Media B), and were suspended in Media B to give a cell density of $5 \times 10^4$ cells/mL. CHO-S-SFM II medium (GIBCO) prepared without the addition of human insulin was used as Media B. 100 µl/well of the cell suspension, 80 µL/well of Media B, and 20 µl/well of human insulin appropriately diluted in 10 mM HCl solution that contained 0.1% bovine serum albumin (SIGMA) were dispensed into the wells of a 96-well microtiter plate (flat bottom, Falcon), and were cultured for 72 hours in a $CO_2$ incubator ($CO_2$ concentration, 5%). After the culture, 20 µl/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of change in absorbance after the two-hour incubation on the vertical axis and the concentrations of human insulin on the horizontal axis, cell line ING#139 that had a high sensitivity to human insulin was selected and used as chimeric insulin receptor-expressing cell line ING (FIG. 7).

(1-7) Platelet-Derived Growth Factor (Hereinafter Referred to as PDGF) Receptor

A chimeric receptor cDNA was constructed by linking cDNA fragments encoding the β chain (from the 1st to the 531st amino acid residues; Gronwald, RGK. et al. (1988) Proc. Natl. Acad. Sci. USA. 85, 3435-3439) of human PDGF receptor, and the transmembrane and intracellular domains (from the 602nd to the 813th amino acid residues; Fukunaga, R. et al. (1990) Cell 61, 341-350) of mouse G-CSF receptor. The cDNA was inserted downstream of the HEF1α promoter of the mammalian expression vector pCV to construct chimeric receptor-expression vector pCV-cPDGFR. pCV-cPDGFR was linearized with Pvu I (Takara Shuzo), extracted with phenol and chloroform, and purified by ethanol precipitation.

The linearized expression gene vector was introduced into mouse Ba/F3 cells using an electroporation apparatus (Gene Pulser: Bio Rad). The Ba/F3 cells were washed twice with Dulbecco's PBS (hereinafter referred to as PBS), and then were suspended in PBS to give a cell density of about $1 \times 10^7$ cells/mL. 20 µg of the linearized expression vector DNA was added to 0.8 mL of this suspension, transferred into a cuvette (Bio Rad) for electroporation, and pulsed with a capacitance of 960 µF at 0.33 kV.

After leaving standing for about 10 min at room temperature, the cells treated by electroporation were suspended in Media A, and were seeded on a 96-well microtiter plate (flat bottom, Falcon) at 100 µL/well. 100 µL/well Media A containing 40 ng/mL human PDGF-BB (Genzyme) was added, and the cells were cultured in a $CO_2$ incubator ($CO_2$ concentration, 5%) RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells with a single colony and subcultured in Media A that contained 20 ng/mL human PDGF-BB.

Figure 8:
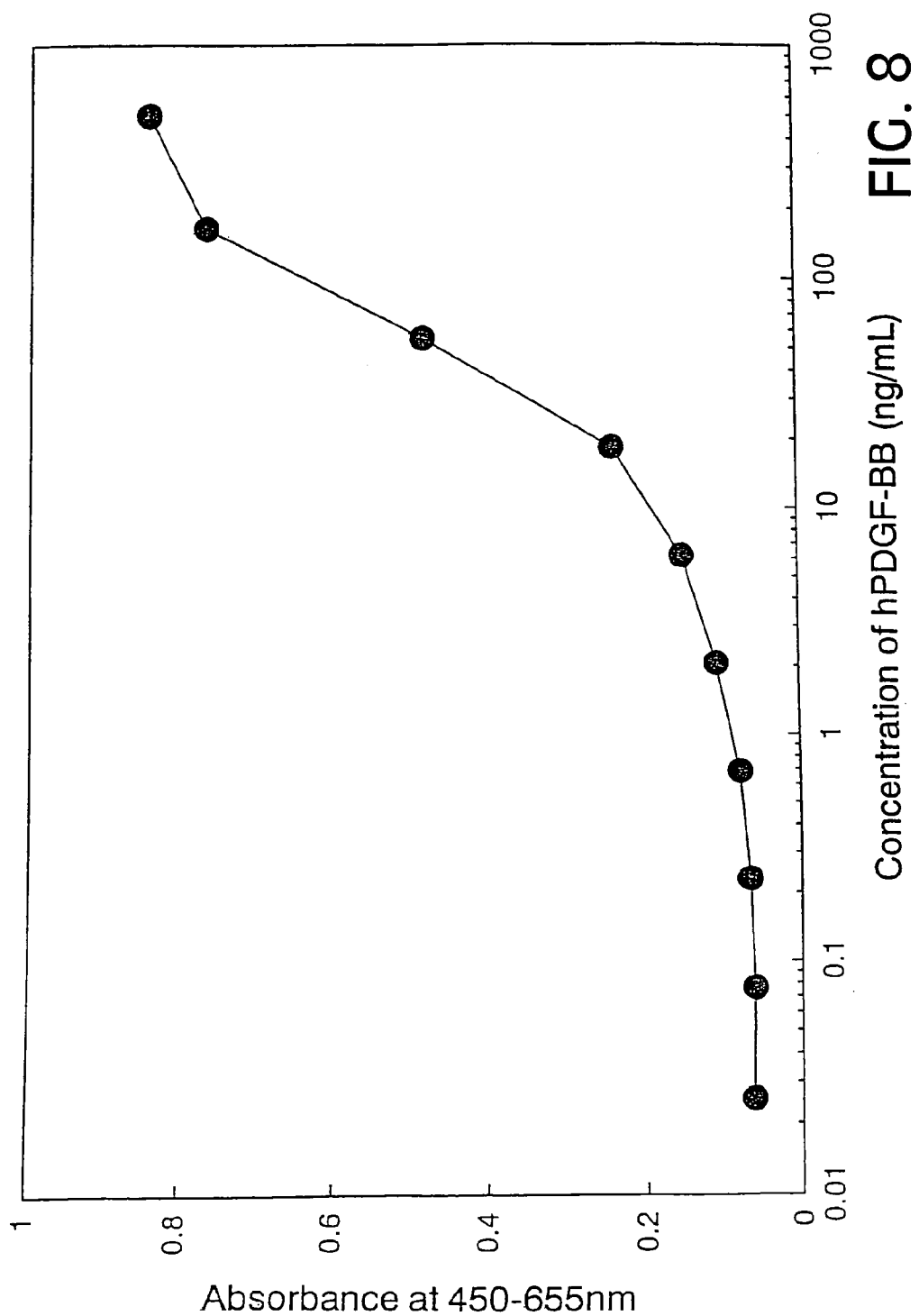
FIG. 8 depicts the response of the chimeric PDGF receptor-expressing Ba/F3 cell line PDG against human PDGF-BB. An evident growth reaction against human PDGF-BB was observed at concentrations of 30 ng/mL or more.

The cells were washed twice with Media A, and were suspended in Media A to give a cell density of $5 \times 10^4$ cells/mL. 50 µl/well of the cell suspension and 50 µL/well human PDGF-BB appropriately diluted in Media A were dispensed into the wells of a 96-well microtiter plate (flat bottom, Falcon), and were cultured for 70 hours in a $CO_2$ incubator ($CO_2$ concentration, 5%). After the culture, 10 µL/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of change in absorbance after the two-hour incubation on the vertical axis and the concentrations of human PDGF-BB on the horizontal axis, cell line PDG#35 that had a high sensitivity to human PDGF-BB was selected and used as chimeric PDGF receptor-expressing cell line PDG (FIG. 8).

(1-8) Interferon (Hereinafter Referred to as IFN) α/β Receptor

Chimeric receptor cDNAs were constructed by linking cDNA fragments encoding extracellular domain of the α chain (AR1) (from the 1st to the 436th amino acid residues; Uze, G. et al. (1990) Cell 60, 225-234) and the α/β chain (AR2;β) (from the 1st to the 243rd amino acid residues; Novick, D. et al. (1994) Cell 77, 391-400) of human IFN α/β receptor with the transmembrane and intracellular domains (from the 602nd to the 813th amino acid residues; Fukunaga, R. et al. (1990) Cell 61, 341-350) of mouse G-CSF receptor, respectively. These cDNAs were inserted downstream of the HEF1α promoter of the mammalian expression vector pCV to construct chimeric receptor-expression vectors, IFGα/pCV and IFGβ/pCV, respectively. Both IFGα/pCv and IFGβ/pCV were linearized with Pvu I (Takara Shuzo), respectively, extracted with phenol and chloroform, and purified by ethanol precipitation.

The linearized expression gene vectors were introduced into mouse Ba/F3 cells using an electroporation apparatus (Gene Pulser: Bio Rad). The Ba/F3 cells were washed twice with Dulbecco's PBS (hereinafter referred to as PBS), and then were suspended in PBS to give a cell density of about $1 \times 10^7$ cells/mL. 10 μg each of linearized IFGα/pCV and IFGβ/pCV was added to 0.8 mL of the suspension, transferred into a cuvette (Bio Rad) for electroporation, and pulsed with a capacitance of 960 μF at 0.33 kV.

After leaving standing for about 10 mm at room temperature, the cells were suspended in Media A, and were seeded on a 96-well microtiter plate (flat bottom, Falcon) at 100 μL/well. 100 μL/well Media A containing 1,000 U/mL human IFNα (CALBIOCHEM) was added, and the cells were cultured in a CO2 incubator (CO2 concentration, 5%). RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells with a single colony and subcultured in Media A containing 1,000 U/mL IFNα.

The cells were washed twice with Media A, and were suspended in Media A to give a cell density of $5 \times 10^4$ cells/mL. 50 μl/well cell suspension and 50 μL/well of human IFNa appropriately diluted in Media A were dispensed into the wells of a 96-well microtiter plate (flat bottom, Falcon), and were cultured for 72 hours in a $CO_2$ incubator ($CO_2$ concentration, 5%). After the culture, 10 μL/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of changes in absorbance measured after the two-hour incubation on the vertical axis and the concentrations of human IFNα on the horizontal axis, cell line IFG#A01 that had a high sensitivity to human IFNα was selected and used as chimeric IFNα receptor-expressing cell line IFG.

Figure 9:
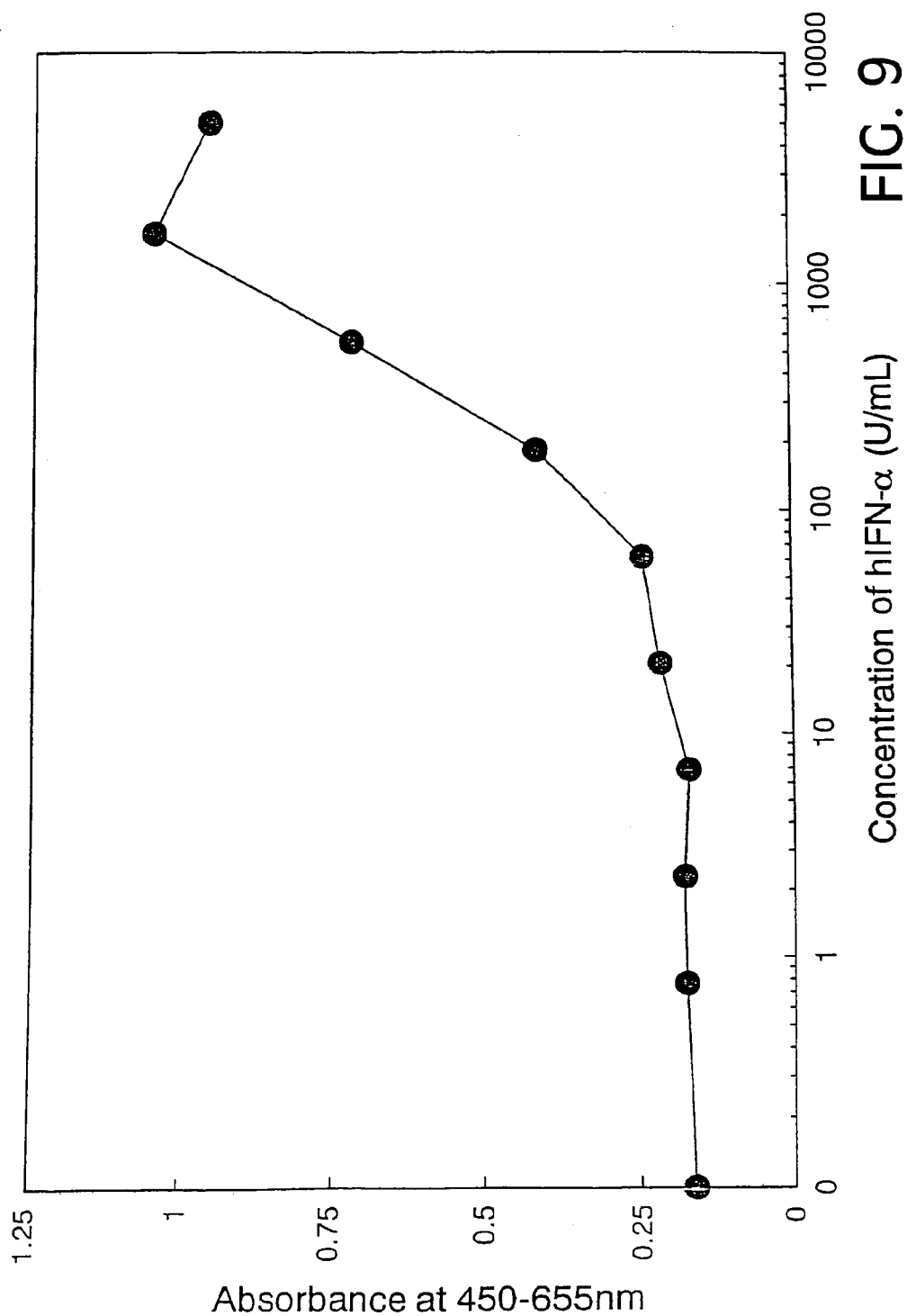
FIG. 9 depicts the response of the chimeric IFNα receptor-expressing Ba/F3 cell line IFG against human IFNα. An evident growth reaction against human IFNα was observed at concentrations of 200 U/mL or more.
Figure 10:
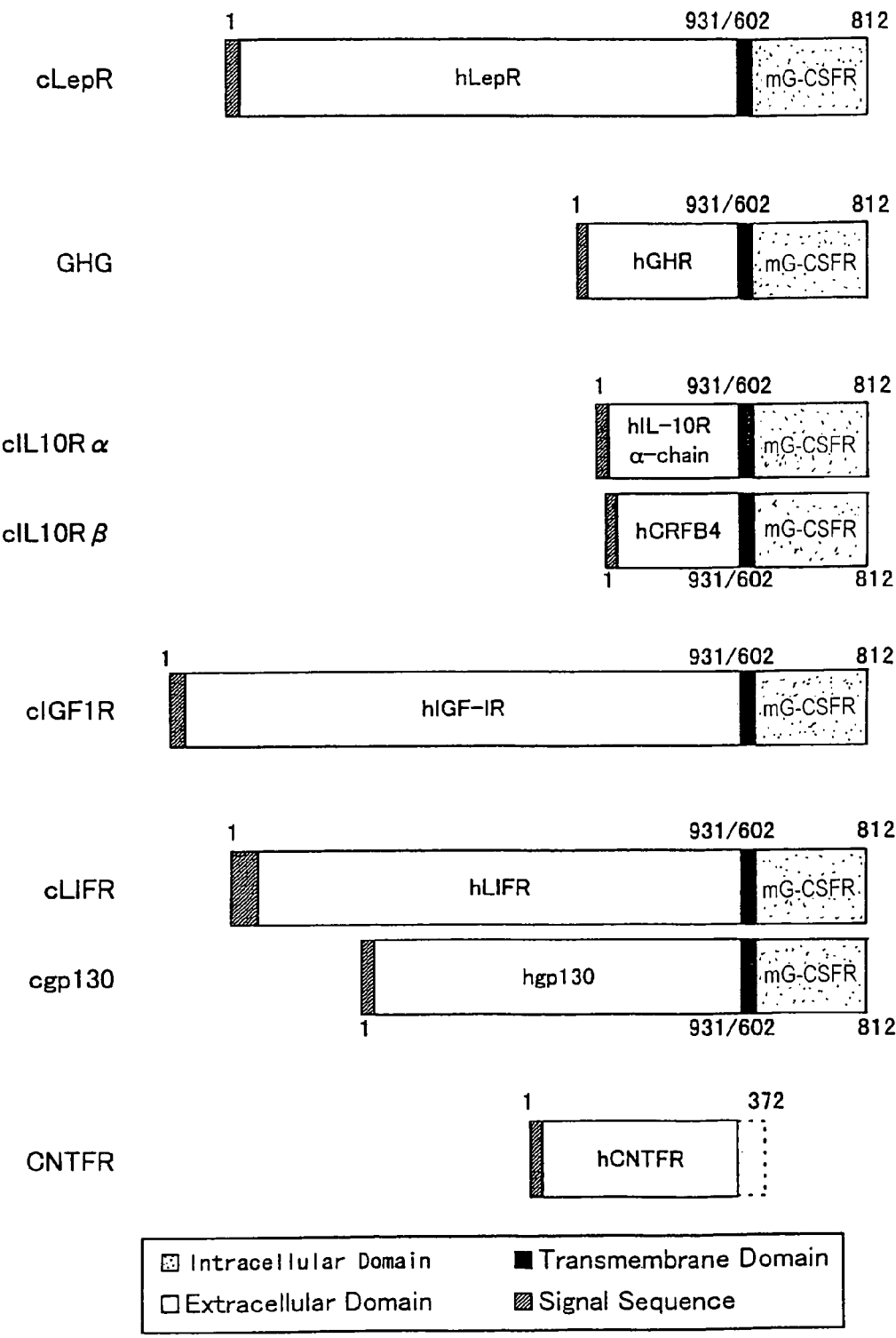
FIG. 10 depicts the amino acid sequences of the used chimeric receptor molecules. The extracellular domains were derived from various human receptors, and the intracellular domains from mouse G-CSF receptor (from the 602nd to the 812th amino acid residues of mouse G-CSF receptor).

The IFNα/β receptor has been known to form a heterodimer, not a homodimer, to transmit the signal. According to the present experiment, even if the intracellular domain of a heterodimer forming receptor was replaced with that of a homodimer forming receptor (represented by the G-CSF receptor), the chimeric receptor induced signal transduction and the response of ligands could be detected as the cell growing activity (FIG. 9).

(1-9) Leptin Receptor

A chimeric receptor cDNA was constructed by linking cDNA fragments encoding the extracellular domain (from the 1st to the 839th amino acid residues; Tartaglia, L A. et al. (1995) Cell, 83, 1263-1271) of human leptin receptor, and the transmembrane and intracellular domains (from the 602nd to the 813th amino acid residues; Fukunaga, R. et al. (1990) Cell 61, 341-350) of mouse G-CSF receptor. This cDNA was inserted downstream of the HEF1α promoter of the mammalian expression vector pCV to construct chimeric receptor expression vector pCV-cLepR. pCV-cLepR was linearized with Pvu I (Takara Shuzo), extracted with phenol and chloroform, and purified by ethanol precipitation.

The linearized expression gene vector was introduced into mouse Ba/F3 cells (purchased from RIKEN; Cell No.: RCB0805) using an electroporation apparatus (Gene Pulser: Bio Rad) The Ba/F3 cells were washed twice with Dulbecco's PBS (hereinafter referred to as PBS), and then were suspended in PBS to give a cell density of about $1 \times 10^7$ cells/mL. 10 μg of the linearized expression vector DNA was added to 0.8 mL of this suspension, transferred into a cuvette (Bio Rad) for electroporation, and pulsed with a capacitance of 960 μF at 0.33 kV.

After leaving standing for 10 min at room temperature, the cells treated by electroporation were suspended in 50 mL Media A, and were seeded on five 96-well microtiter plates (flat bottom, Falcon) at 100 μL/well. 100 μL/well Media A containing 10 ng/mL human leptin (Genzyme) was added, and the cells were cultured in a $CO_2$ incubator ($CO_2$ concentration, 5%). RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells of a single colony and subcultured in Media A containing 10 ng/mL human leptin.

Figure 11:
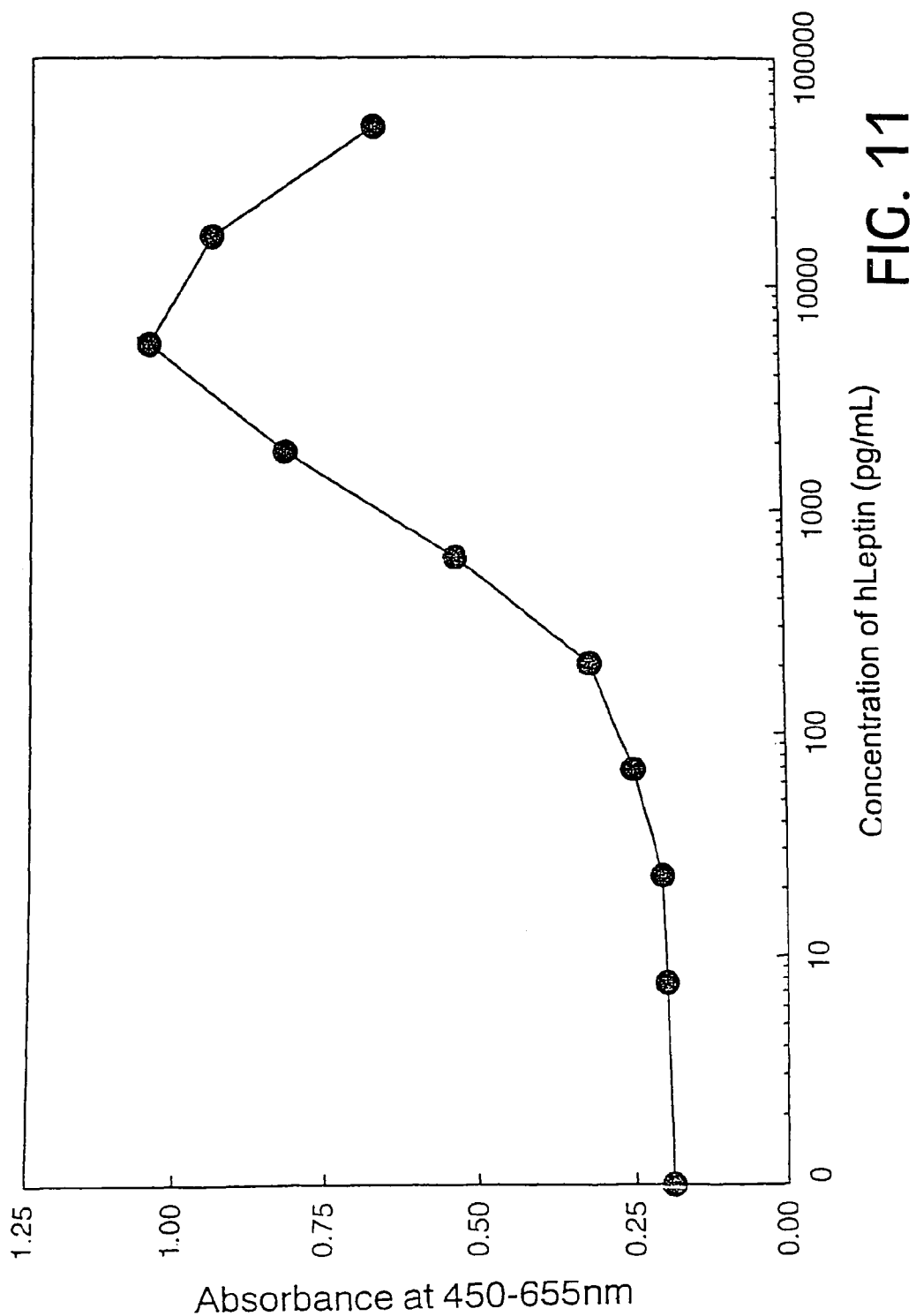
FIG. 11 depicts the response of the chimeric leptin receptor-expressing Ba/F3 cell line LPG against human leptin. An evident growth reaction against human leptin was observed at concentrations of 0.2 ng/mL or more.

The cells were washed twice with Media A, and were suspended in Media A to give a cell density of $5 \times 10^4$ cells/mL. 50 μl/well of the cell suspension and 50 μL/well of human leptin appropriately diluted in Media A were dispensed into the wells of a 96-well microtiter plate (flat bottom, Falcon), and were cultured for 72 hours in a $CO_2$ incubator ($CO_2$ concentration, 5%). After the culture, 10 μL/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of changes in the absorbance measured after the two-hour incubation on the vertical axis and the concentrations of human leptin on the horizontal axis, cell line LPG#51 that had a high sensitivity to human leptin was selected, and was used as chimeric leptin receptor-expressing cell line LPG. The subculture of the cell line was conducted in the presence of 1 ng/mL human leptin. An obvious growth reaction against leptin could be observed at a concentration of 0.2 ng/mL or more of human leptin (FIG. 11).

(1-10) Growth Hormone (Hereinafter Referred to as GH) Receptor

A chimeric receptor cDNA was constructed by linking cDNA fragments encoding the extracellular domain (from the 18th to the 246th amino acid residues; Leung, D W. et al. (1987) Nature 330, 537-543) of human GH receptor, and the transmembrane and intracellular domains (from the 602nd to the 813th amino acid residues; Fukunaga, R. et al. (1990) Cell 61, 341-350) of mouse G-CSF receptor. This cDNA was inserted downstream of the EF1α promoter of the mammalian expression vector pCV to construct chimeric receptor-expression vector GHG/pCV. GHG/pCV was linearized with Pvu I (Takara Shuzo), extracted with phenol and chloroform, and purified by ethanol precipitation.

The linearized expression gene vector was introduced into mouse Ba/F3 cells (purchased from RIKEN; Cell No.: RCB0805) using an electroporation apparatus (Gene Pulser: Bio Rad). The Ba/F3 cells were washed twice with Dulbecco's PBS (hereinafter referred to as PBS), and then were suspended in PBS to give a cell density of about $1\times10^7$ cells/mL. 10 µg of the linearized expression vector DNA was added to 0.8 mL of this suspension, transferred into a cuvette (Bio Rad) for electroporation, and pulsed with a capacitance of 960 µF at 0.33 kV.

After leaving standing for about 10 min at room temperature, the cells treated by electroporation were suspended in 50 mL Media A, and were seeded on five 96-well microtiter plates (flat bottom, Falcon) at 100 µL/well. 100 µL/well Media A that contained 200 µIU/mL human GH (Genotropin (R): Pharmacia & Upjohn) was added, and the cells were cultured in a $CO_2$ incubator ($CO_2$ concentration, 5%). RPMI1640 (GIBCO) supplemented with 10% fetal bovine serum (HyClone), 100 U/mL penicillin, and 0.1 mg/mL streptomycin (GIBCO) was used as Media A. About one week after the start of the culture, the cells were observed under a microscope, cells were collected from wells of a single colony and subcultured in Media A containing 500 µIU/mL human GH.

Figure 12:
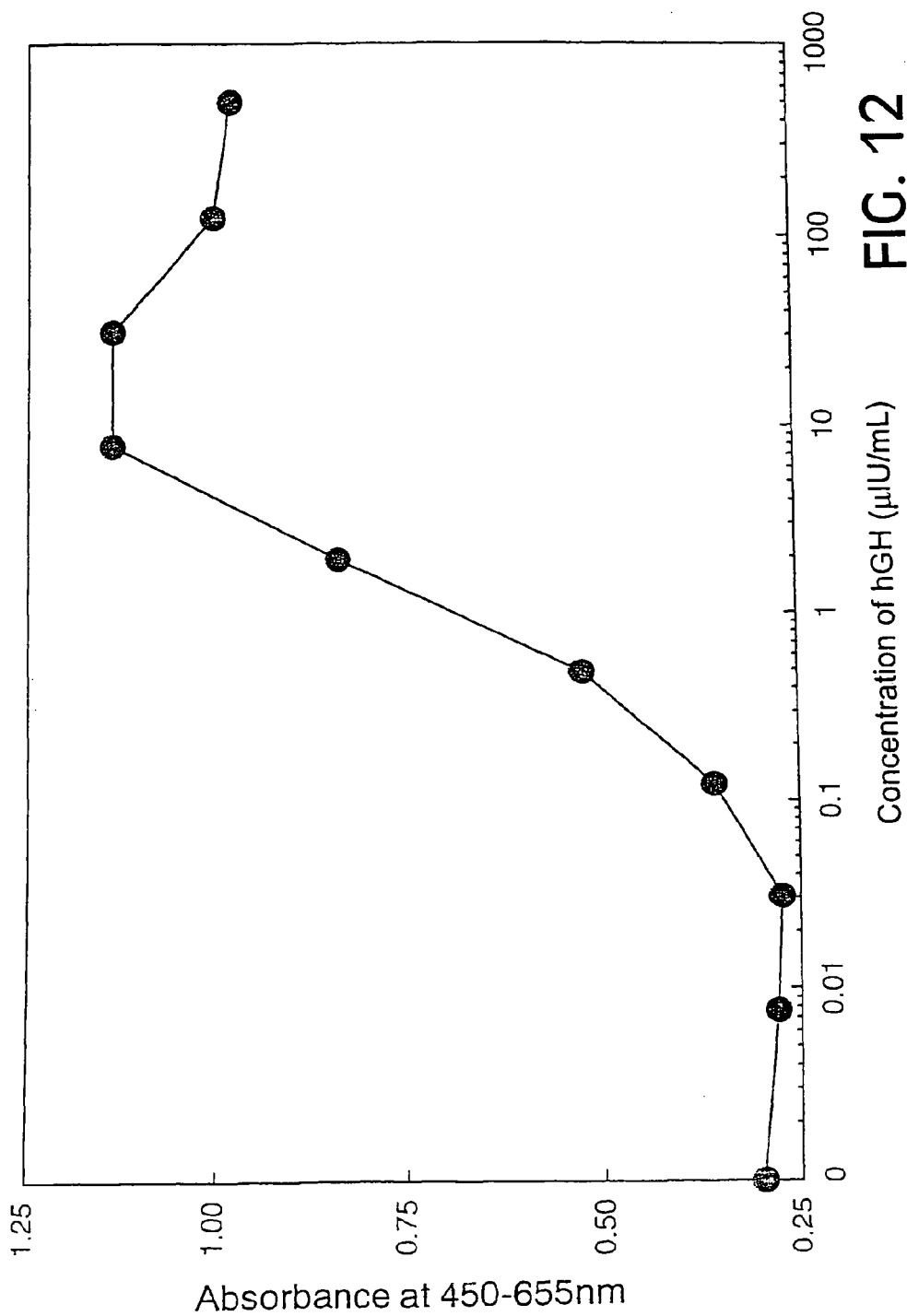
FIG. 12 depicts the response of the chimeric GH receptor-expressing Ba/F3 cell line GHG against human GH. An evident growth reaction against human GH was observed at concentrations of 0.3 μIU/mL or more.

The cells were washed twice with Media A, and were suspended in Media A to give a cell density of $5\times10^4$ cells/mL. 50 µl/well cell suspension and 50 µL/well human GH appropriately diluted in Media A were dispensed into the wells of a 96-well microtiter plate (flat bottom, Falcon), and were cultured for 72 hours in a $CO_2$ incubator ($CO_2$ concentration, 5%). After the incubation, 10 µL/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of change in the absorbance measured after the two-hour incubation on the vertical axis and the concentrations of human GH on the horizontal axis, cell line GHG#11 that had a high sensitivity to human GH was selected, and was used as chimeric GH receptor-expressing cell line GHG. This cell line was subcultured in the presence of 20 µIU/mL human GH. At a concentration of 0.3 µIU/mL or more, an obvious growth reaction against human GH was observed (FIG. 12).

(1-11) Interleukin 10 (Hereinafter Referred to as IL-10) Receptor

Chimeric receptor cDNAs were constructed by linking cDNA fragments encoding the α chain (IL-10Rα) (from the 1st to the 235th amino acid residue; Liu, Y. et al. (1994) J. Immunol. 152, 1821-1829) and the hIL-10R subunit (CRFB4; IL-10Rβ) extracellular domain (from the 1st to the 220th amino acid residues; Lutfalla, G. et al. (1993) Genomics 16, 366-373) of human IL-10 receptor with the transmembrane and intracellular domains (from the 602nd to the 813th amino acid residues; Fukunaga, R. et al. (1990) Cell 61, 341-350) of mouse G-CSF receptor, respectively. These constructs were inserted downstream of the HEF1α promoter of the mammalian expression vector pCV to construct chimeric receptor-expression vectors, pCV -cIL10Rα and pCV-cIL10Rβ, respectively. pCV-cIL10Rα and pCV-cIL10Rβ were linearized with Pvu I (Takara Shuzo), respectively, extracted with phenol and chloroform, and purified by ethanol precipitation.

The linearized expression gene vectors were introduced into mouse Ba/F3 cells, respectively, using an electroporation apparatus (Gene Pulser: Bio Rad). The Ba/F3 cells were washed twice with Dulbecco's PBS (hereinafter referred to as PBS), and then were suspended in PBS to give a cell density of about $1\times10^7$ cells/mL. 10 µg each of linearized expression vector DNA, pCv-cIL10Rα and pCV-cIL10Rβ, was added to 0.8 mL of this suspension, transferred into a cuvette (Bio Rad) for electroporation, and pulsed with a capacitance of 960 µF at 0.33 kV.

After leaving standing for about 10 min at room temperature, the cells treated by electroporation were suspended in 50 mL Media A, and were seeded on five 96-well microtiter plates (flat bottom, Falcon) at 100 µL/well. 100 µL/well Media A that contained 10 ng/mL of human IL-10 (Genzyme) was added, and the cells were cultured in a $CO_2$ incubator ($CO_2$ concentration, 5%). RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells with a single colony and subcultured in Media A containing 5 ng/mL human IL-10.

Figure 13:
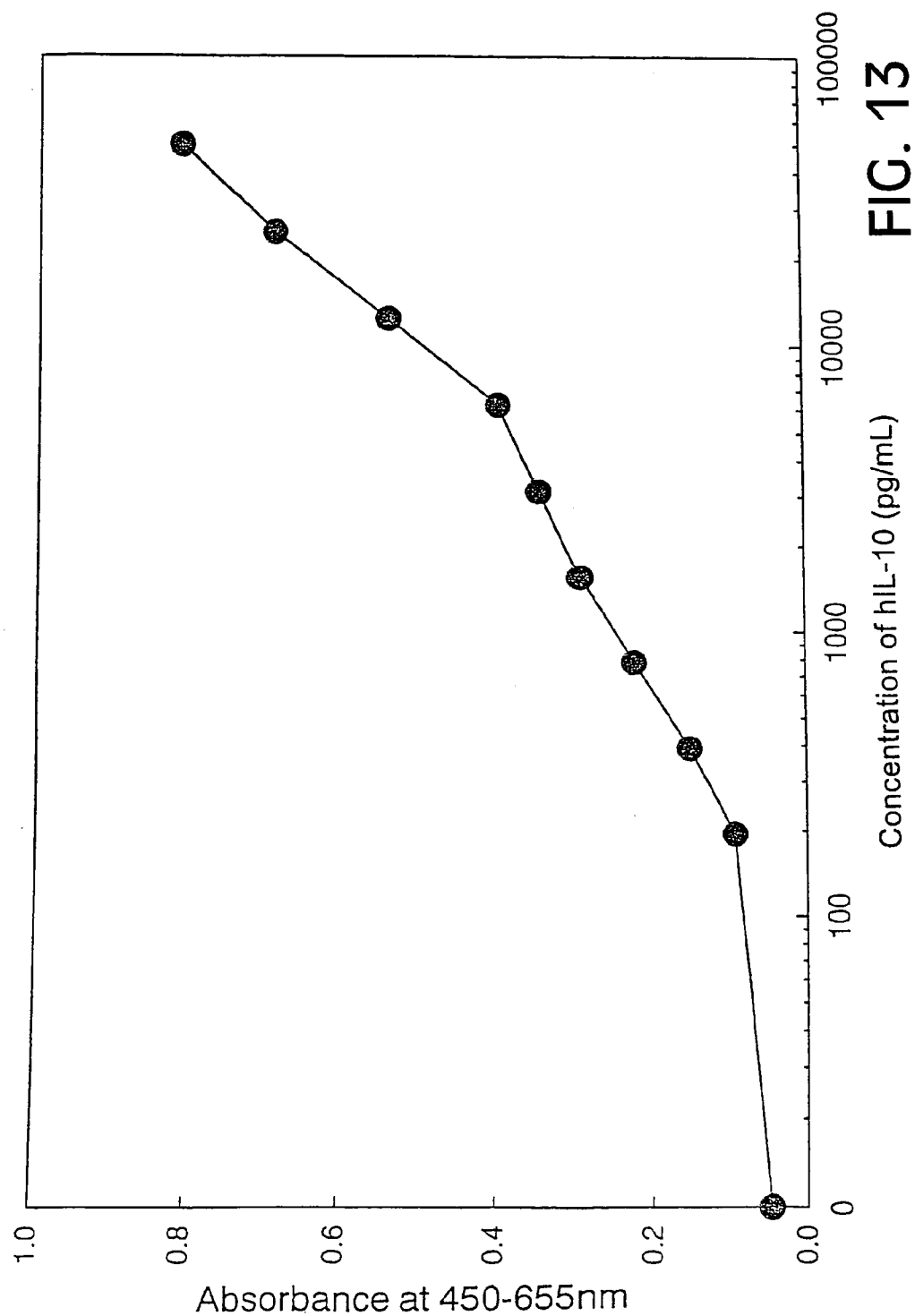
FIG. 13 depicts the response of the chimeric IL-10 receptor-expressing Ba/F3 cell line 10G against human IL-10. An evident growth reaction against human IL-10 was observed at concentrations of 0.5 ng/mL or more.

The cells were washed twice with Media A, and were suspended in Media A to give a cell density of $5\times10^4$ cells/mL. 50 µl/well cell suspension and 50 µL/well human IL-10 appropriately diluted in Media A were dispensed into wells of a 96-well microtiter plate (flat bottom, Falcon), and were cultured for 72 hours in a $CO_2$ incubator ($CO_2$ concentration, 5%). After the culture, 10 µL/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of changes in absorbance measured after the two-hour incubation on the vertical axis and the concentrations of human IL-10 on the horizontal axis, cell line 10G#10 that had a high sensitivity to human IL-10 was selected and used as chimeric IL-10 receptor-expressing cell line 10G. This cell line was subcultured in the presence of 1 ng/mL human IL-10. At a concentration of 0.5 ng/mL or more, an obvious growth reaction against human IL-10 was observed (FIG. 13).

(1-12) Insulin-Like Growth Factor I (Hereinafter Referred to as IGF-I) Receptor

A chimeric receptor cDNA was constructed by linking cDNA fragments encoding the extracellular domain (from the 1st to the 931st amino acid residues; Ullrich, A. et al. (1986) EMBO J., 5, 2503-2512) of human IGF-I receptor, and the transmembrane and intracellular domains (from the 602nd to the 813th amino acid residues; Fukunaga, R. et al. (1990) Cell 61, 341-350) of mouse G-CSF receptor. This construct was inserted downstream of the HEF1α promoter of the mammalian expression vector pCV to construct chimeric receptor-expression vector pCV-cIGF1R. pCV-cIGF1R was linearized with Pvu I (Takara Shuzo), extracted with phenol and chloroform, and purified by ethanol precipitation.

The linearized expression vector was introduced into mouse Ba/F3 cells using an electroporation apparatus (Gene Pulser: Bio Rad). The Ba/F3 cells were washed twice with Dulbecco's PBS (hereinafter referred to as PBS), and then were suspended in PBS to give a cell density of about $1\times10^7$ cells/mL. 20 μg linearized expression vector DNA was added to 0.8 mL of this suspension, transferred into a cuvette (Bio Rad) for electroporation, and pulsed with a capacitance of 960 μF at 0.33 kV.

After leaving standing for about 10 min at room temperature, the cells treated by electroporation were suspended in 40 mL Media A, and were seeded on four 96-well microtiter plates (flat bottom, Falcon) at 100 μL/well. 100 μL/well Media A that contained 40 ng/mL human IGF-I (Genzyme) was added, and the cells were cultured in a $CO_2$ incubator ($CO_2$ concentration, 5%). RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells of a single colony and subcultured in Media A containing 20 to 50 ng/mL human IGF-I.

Figure 14:
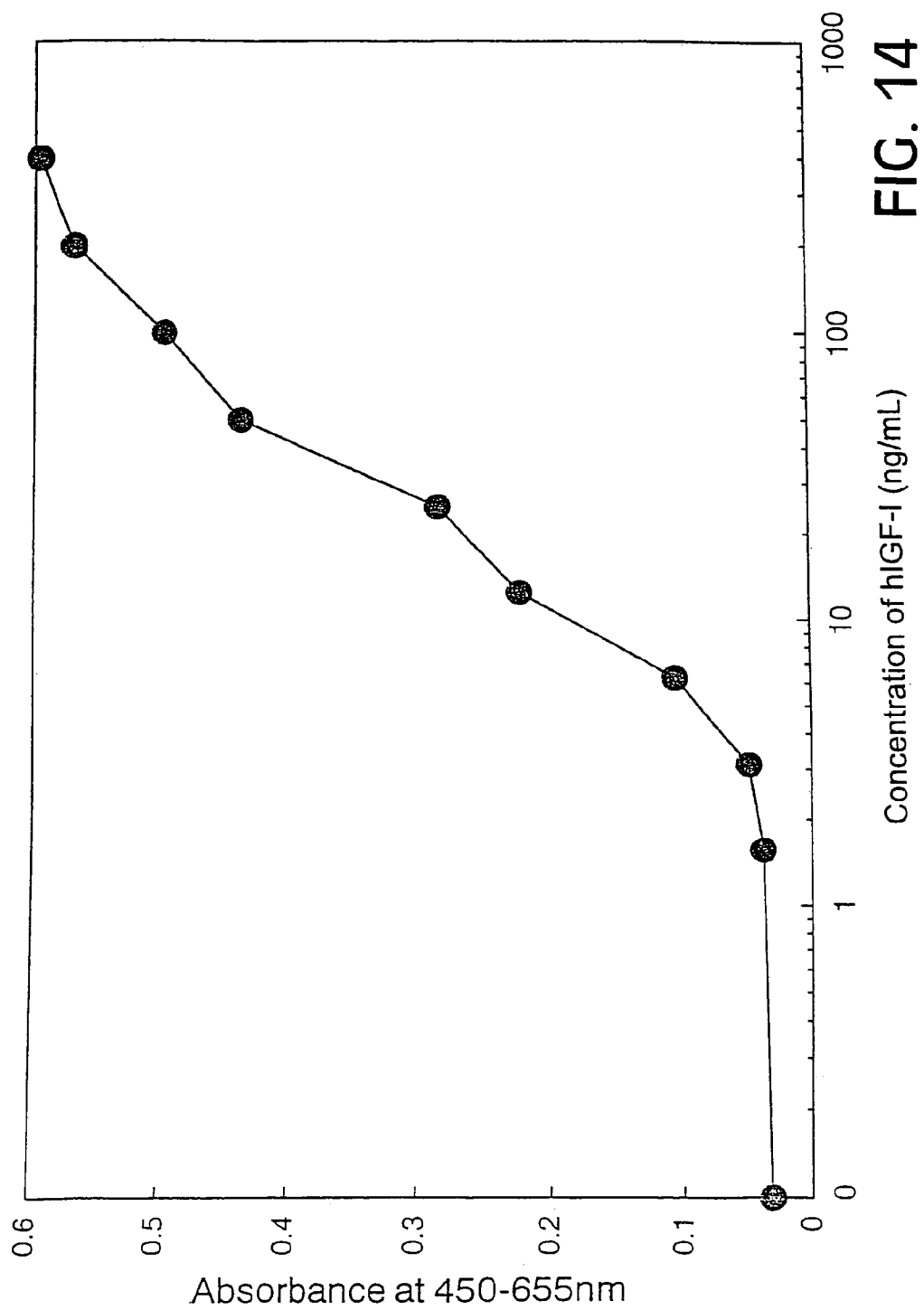
FIG. 14 depicts the response of the chimeric IGF-I receptor-expressing Ba/F3 cell line IGG against human IGF-I. An evident growth reaction against human IGF-I was observed at concentrations of 10 ng/mL or more.

The cells were washed twice with media without human insulin (hereinafter referred to as Media B), and were suspended in Media B to give a cell density of 5×104 cells/mL. CHO-S-SFM II medium (GIBCO) without the addition of human insulin was used as Media B. 50 μl/well cell suspension and 50 μL/well human IGF-I appropriately diluted with Media B were dispensed into the wells of a 96-well microtiter plate (flat bottom, Falcon), and were cultured for 72 hours in a CO2 incubator (CO2 concentration, 5%). After the culture, 10 μL/well WST-8 reagent (Cell Count Reagent SF; Nacalai Tesque was added, and pre-reaction absorbance at a measurement wavelength of 450 nm and a control wavelength of 655 nm was measured using microplate reader (Model 3550, Bio Rad). The plate was incubated for two hours in a CO2incubator (CO2 concentration, 5%), and post-reaction absorbance was measured as above. Based on the cell growth activity determined by the number of viable cells by plotting the amount of changes in absorbance measured after the two-hour incubation on the vertical axis and the concentrations of human IGF-I on the horizontal axis, cell line IGG#06 that had a high sensitivity to human IGF-I was selected and used as chimeric IGF-I receptor-expressing cell line IGG. This cell line was subcultured in the presence of 50 ng/mL human IGF-I. At a concentration of 10 ng/mL or more, an obvious growth reaction to human IGF-I was observed (FIG. 14).

(1-13) Leukemia Inhibitory Factor (Hereinafter Referred to as LIF) Receptor

Chimeric receptor DNAs were constructed by linking cDNA fragments encoding human LIF receptor (from the 1st to the 833rd amino acid residues; Gearing, D P. et al. (1988) EMBO J., 10, 2839-2848) and human gp130 (from the 1st to the 619th amino acid residues; Hibi, M. et al. (1990) Cell, 63, 1149-1157) with the transmembrane and intracellular domains (from the 602nd to the 813th amino acid residues; Fukunaga, R. et al. (1990) Cell 61, 341-350) of mouse G-CSF receptor, respectively. These constructs were inserted downstream of the HEF1α promoter of the mammalian expression vector pCV to construct chimeric receptors expression vectors, pCV-cLIFR and pCV-cgp130, respectively. pCV-cLIFR and pCV-cgp130 were linearized with Pvu I (Takara Shuzo), respectively, extracted with phenol and chloroform, and purified by ethanol precipitation.

The linearized expression vectors were introduced into mouse Ba/F3 cells using an electroporation apparatus (Gene Pulser: Bio Rad). The Ba/F3 cells were washed twice with Dulbecco's PBS (hereinafter referred to as PBS), and then were suspended in PBS to give a cell density of about $1\times10^7$ cells/mL. 20 μg each of the linearized expression vector DNA, pCV-cLIFR and pCV-cgp130, was added to 0.8 mL of this suspension, transferred into a cuvette (Bio Rad) for electroporation, and pulsed with a capacitance of 960 μF at 0.33 kV.

After leaving standing for about 10 min at room temperature, the cells treated by electroporation were suspended in 40 mL of Media A, and were seeded on four 96-well microtiter plates (flat bottom, Falcon) at 100 μL/well. 100 μL/well Media A that contained 10 ng/mL human LIF (Genzyme) was added, and the cells were cultured in a $CO_2$ incubator ($CO_2$ concentration, 5%). RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells with a single colony and subcultured in Media A containing 5 ng/mL human LIF.

Figure 15:
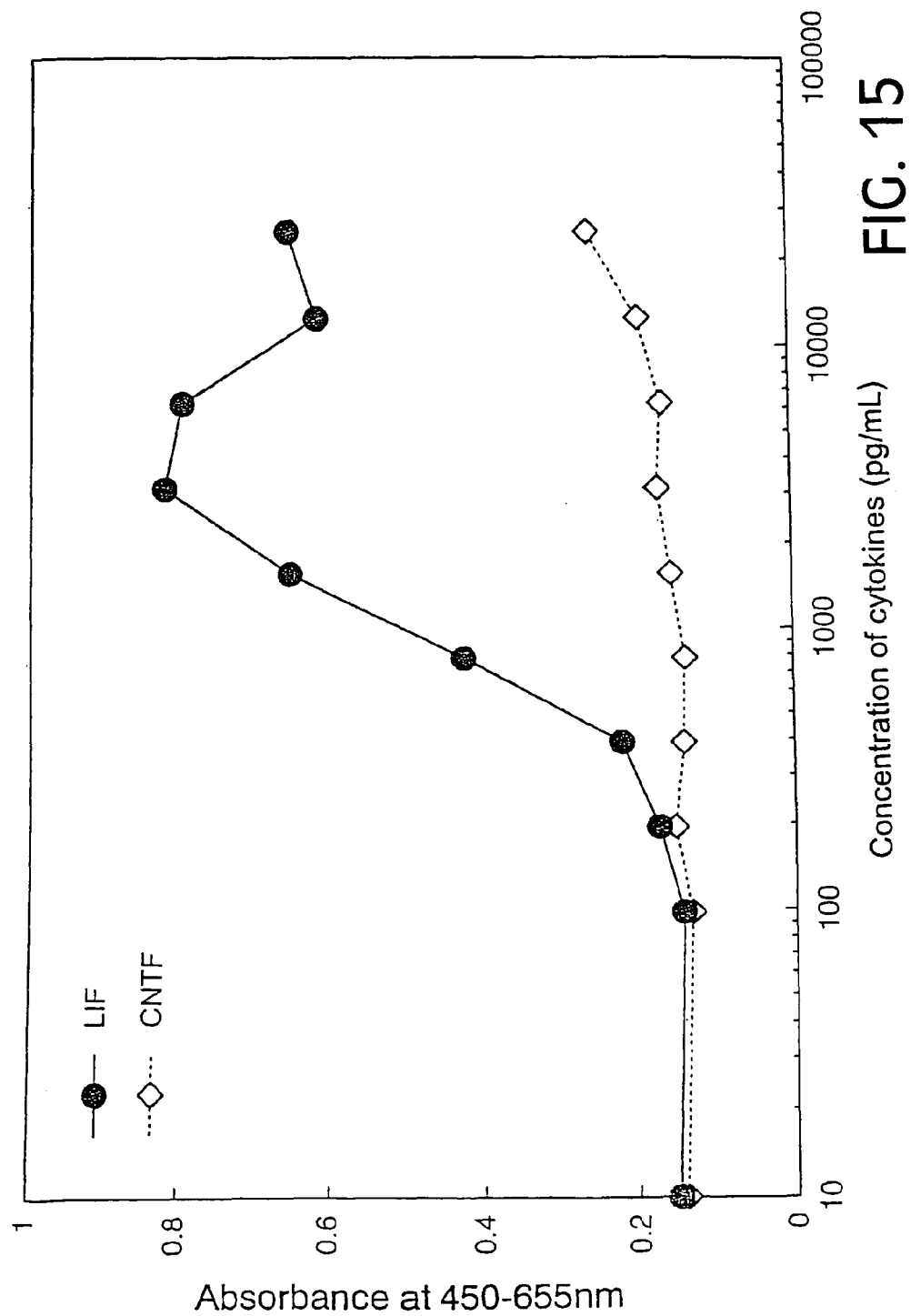
FIG. 15 depicts the response of the chimeric LIF receptor-expressing Ba/F3 cell line LIG against human LIF. An evident growth reaction against human LIF was observed at concentrations of 0.4 ng/mL or more, but not in the presence of human CNTF at concentrations of 10 ng/mL or less.

The cells were washed twice with Media A, and were suspended in Media A to give a cell density of $5\times10^4$ cells/mL. 50 μl/well cell suspension and 50 μL/well human LIF or CNTF, each appropriately diluted in Media A, were dispensed into the wells of a 96-well microtiter plate (flat bottom, Falcon), and were cultured for 72 hours in a $CO_2$ incubator ($CO_2$ concentration, 5%). After the culture, 10 μL/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of changes in absorbance measured after the two-hour incubation on the vertical axis and the concentrations of human LIF on the horizontal axis, cell line LIG#47 that had a high sensitivity to human LIF was selected and used as chimeric LIF receptor-expressing cell line LIG. This cell line was subcultured in the presence of 1 ng/mL human LIF. At a concentration of 0.4 ng/mL or more, an obvious growth reaction to human LIF could be observed (FIG. 15).

(1-14) Ciliary Neurotrophic Factor (Hereinafter Referred to as CNTF) Receptor

Human CNTF receptor (from the 1st to the 372nd amino acid residues; Davis, S. et al. (1991) Science, 253, 59-63) cDNA was cloned downstream of the HEF1α promoter of a mammalian expression vector, pCV, to construct human CNTF receptor (CNTFR) expression vector, pCV-CNTFR. pCV-CNTFR was linearized with Pvu I (Takara Shuzo), extracted with phenol and chloroform, and purified by ethanol precipitation.

The linearized expression gene vector was introduced into the chimeric LIF receptor-expressing cell line LIG (see section 1-13) using an electroporation apparatus (Gene Pulser:

Bio Rad). The LIG cells were washed twice with Dulbecco's PBS (hereinafter referred to as PBS), and then were suspended in PBS to give a cell density of about $1\times10^7$ cells/mL. 10 μg of linearized pCV-CNTFR was added to 0.8 mL of this suspension, transferred into a cuvette (Bio Rad) for electroporation, and pulsed with a capacitance of 960 μF at 0.33 kV.

After leaving standing for about 10 min at room temperature, the cells treated by electroporation were suspended in 40 mL of Media A, and were seeded on four 96-well microtiter plates (flat bottom, Falcon) at 100 μL/well. 100 μL/well Media A that contained 1 ng/mL human CNTF (Genzyme) was added, and the cells were cultured in a $CO_2$ incubator ($CO_2$ concentration, 5%). RPMI1640 (GIBCO) supplemented with 10% fetal bovine serum (Hyclone), 100 U/mL penicillin, and 0.1 mg/mL streptomycin (GIBCO) was used as Media A. About one week after the start of the culture, the cells were observed under a microscope, cells were collected from wells with a single colony and subcultured in Media A containing 0.5 to 1 ng/mL CNTF.

Figure 16:
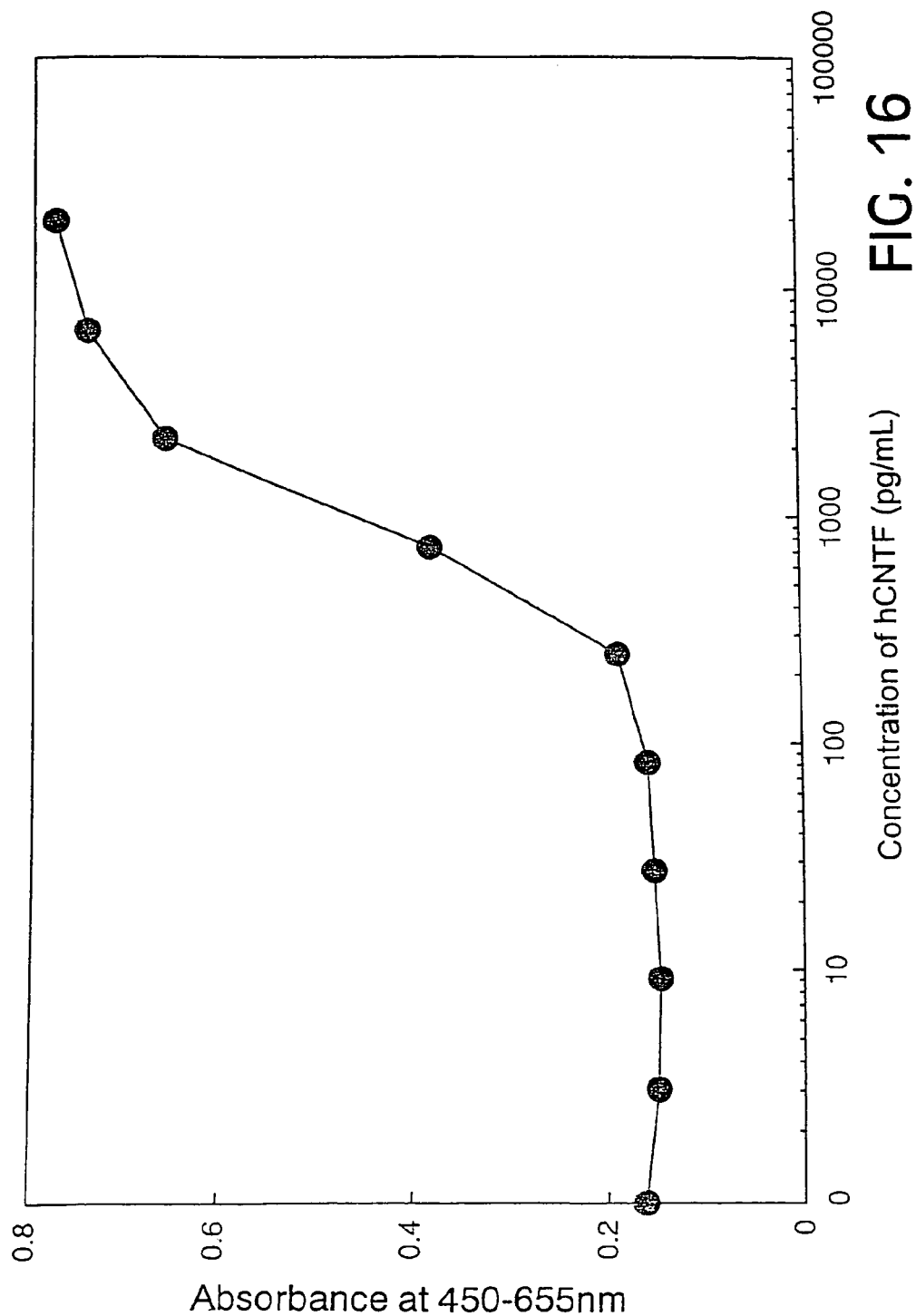
FIG. 16 depicts the response of the chimeric CNTF receptor-expressing Ba/F3 cell line CNG against human CNTF. An evident growth reaction against human CNTF was observed at concentrations of 0.3 ng/mL or more.

The cells were washed twice with Media A, and were suspended in Media A to give a cell density of $5\times10^4$ cells/mL. 50 μl/well cell suspension and 50 μL/well human CNTF appropriately diluted in Media A were dispensed into the wells of a 96-well microtiter plate (flat bottom, Falcon), and were cultured for 72 hours in a $CO_2$ incubator ($CO_2$ concentration, 5%). After the culture, 10 μL/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for two hours in a $CO_2$ incubator ($CO_2$ concentration, 5%), and post-reaction absorbance was measured as above. Based on the cell growth activity determined by the number of viable cells by plotting the amount of changes in absorbance measured after the two-hour incubation on the vertical axis and the concentrations of human CNTF on the horizontal axis, cell line CNG#203 that had a high sensitivity to human CNTF was selected and used as chimeric CNTF receptor-expressing cell line CNG. This cell line was subcultured in the presence of 1 ng/mL human CNTF. At a concentration of 0.3 ng/mL or more, an obvious growth reaction to human CNTF was observed (FIG. 16).

CNTF receptor has been known to form a heterotrimer, not a homodimer, to transmit signal. According to the present experiment, a chimeric receptor of such a heterotrimeric receptor, even if the intracellular domain of the receptor was replaced with that of a homodimeric receptor (represented by the G-CSF receptor), could induce signal transduction and the reactivity of the ligand could be detected as the cell growth activity.

(1-15) Platelet-Derived Growth Factor (Hereinafter Referred to as PDGF) Receptor A chimeric receptor cDNA was constructed by linking cDNA fragments encoding the β chain (from the 1st to the 531st amino acid residues; Gronwald, R G K. et al. (1988) Proc. Natl. Acad. Sci. USA. 85, 3435-3439) of human PDGF receptor and the transmembrane and intracellular domains (from the 602nd to the 813th amino acid residues; Fukunaga, R. et al. (1990) Cell 61, 341-350) of mouse G-CSF receptor. The cDNA was cloned downstream of the EF1α promoter of the mammalian expression vector pCV to construct chimeric receptor-expression vector pCV-cPDGFR. pCV-cPDGFR was linearized with Pvu I (Takara Shuzo), extracted with phenol and chloroform, and purified by ethanol precipitation.

The linearized expression vector was introduced into mouse Ba/F3 cells using an electroporation apparatus (Gene Pulser: Bio Rad). The Ba/F3 cells were washed twice with Dulbecco's PBS (hereinafter referred to as PBS), and then were suspended in PBS to give a cell density of about $1\times10^7$ cells/mL. 20 μg of the linearized expression vector DNA was added to 0.8 mL of this suspension, transferred into a cuvette (Bio Rad) for electroporation, and pulsed with a capacitance of 960 μF at 0.33 kV. After leaving standing for about 10 min at room temperature, the cells treated by electroporation were suspended in Media A, and were seeded on a 96-well microtiter plate (flat bottom, Falcon) at 100 μL/well. 100 μL/well Media A that contained 20 ng/mL human PDGF-BB (Genzyme) was added, and the cells were cultured in a $CO_2$ incubator ($CO_2$ concentration, 5%). RPMI1640 (GIBCO) supplemented with 10 vol % fetal bovine serum (Hyclone), 100 U/mL penicillin, and 0.1 mg/mL streptomycin (GIBCO) was used as Media A. About one week after the start of the culture, the cells were observed under a microscope, cells were collected from wells with a single colony and subcultured in Media A containing 5 ng/mL human PDGF-BB.

Figure 17:
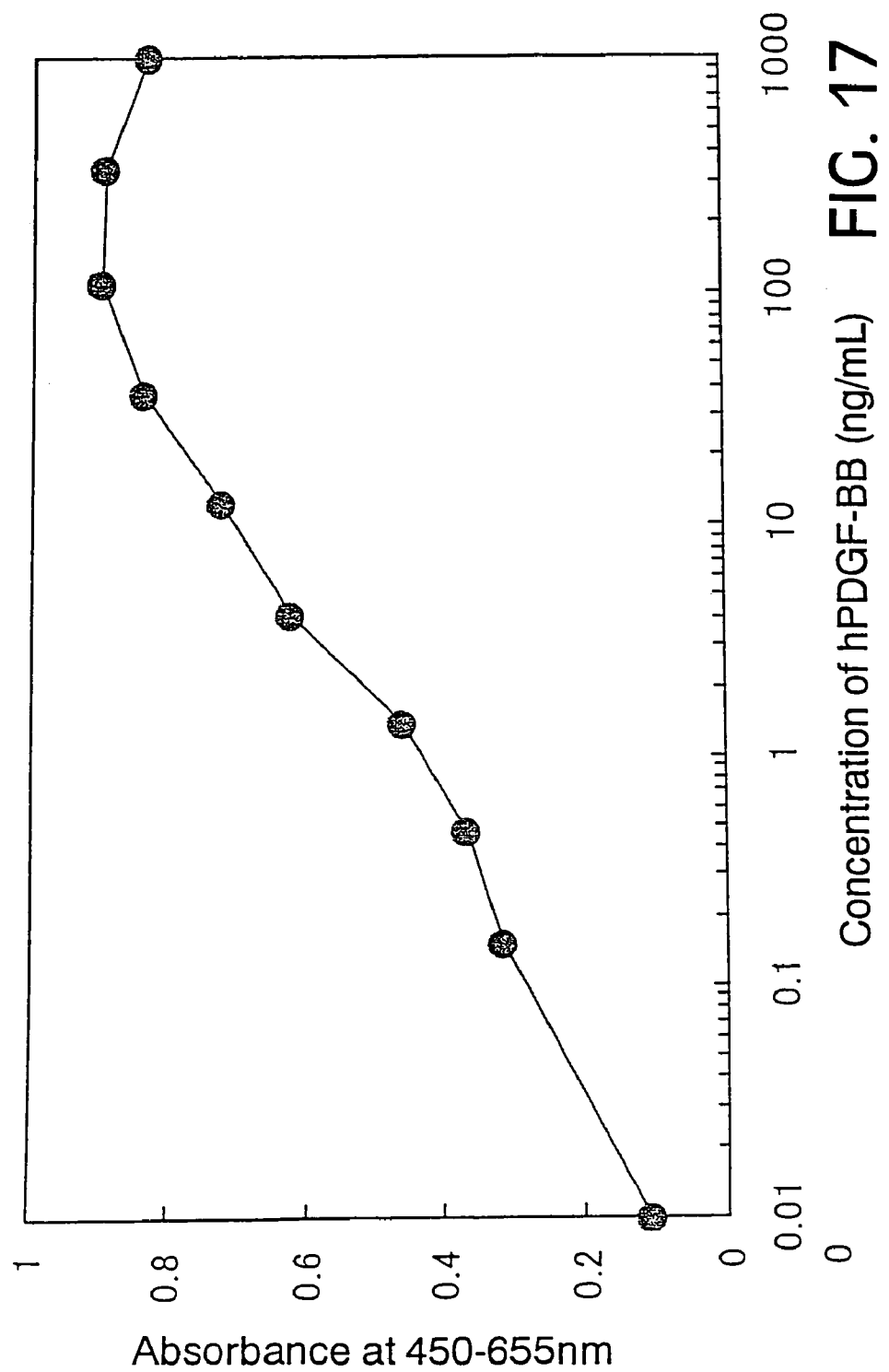
FIG. 17 depicts the response of the chimeric PDGF receptor-expressing Ba/F3 cell line PDG against human PDGF-BB.

The cells were washed twice with Media A, and were suspended in Media A to give a cell density of $5\times10^4$ cells/mL. 50 μl/well cell suspension and 50 μL/well human PDGF-BB appropriately diluted in Media A were dispensed into the wells of a 96-well microtiter plate (flat bottom, Falcon), and were cultured for 72 hours in a $CO_2$ incubator ($CO_2$ concentration, 5%). After the culture, 10 μL/well WST-8 reagent (Cell Count Reagent SF; Nacalai Tesque) was added, and pre-reaction absorbance at a measurement wavelength of 450 nm and a control wavelength of 655 nm was measured using microplate reader (Model 3550, Bio Rad). The plate was incubated for four hours in a $CO_2$ incubator ($CO_2$ concentration, 5%), and post-reaction absorbance was measured as above. Based on the cell growth activity determined by the number of viable cells by plotting the amount of changes in absorbance measured after the 4-hour incubation on the vertical axis and the concentrations of human PDGF-BB on the horizontal axis, cell line PDG#10 that had a high sensitivity to human PDGF-BB was selected and used as chimeric PDGF receptor-expressing cell line PDG (FIG. 17).

EXAMPLE 2

Examination on Cytokine Responses in Mixed Cell Cultures

Mixed culture of the cell lines GFG, EPG, and TPG, which express human G-CSF, EPO, and TPO chimeric receptors, respectively, and their parental cell line Ba/F3 was conducted and their response to various cytokines was examined.

Four cell lines, EPG, GFG, TPG, and the non-recombinant cell Ba/F3, were subcultured in the presence of 1 ng/mL human EPO, 10 ng/mL human G-CSF, 1 ng/mL human TPO (R & D Systems), and 1 ng/mL mouse IL-3 (R & D Systems), respectively. The used human EPO and G-CSF were prepared from recombinant CHO cells, and their titer was 270,000 IU/mg and $1.2\times10^8$ IU/mg, respectively. The cells were washed twice with RPMI1640 media containing 2% fetal bovine serum, and then were suspended in RPMI1640 containing 10% fetal bovine serum. The four cell lines were mixed by adjusting each of the cell lines to $4\times10^4$ cells/mL ($16\times10^4$ cells/mL in total) for the mixed culture, and, for individual cultures, cells were prepared at $4\times10^4$ cells/mL. 100 μL each of the cells were independently seeded on a 96-well microtiter plate (flat bottom, Falcon). After adding 100 μL/well each of appropriately diluted cytokines, the cultures were cultured for 72 hours in a $CO_2$ incubator (5% $CO_2$ concentration). After the culture, 10 μL/well WST-8 reagent (Cell Count Reagent SF; Nacalai Tesque) was added, and pre-reaction absorbance at a measurement wavelength of 450 nm and a control wavelength of 655 nm was measured using a microplate reader (Model 3550, Bio Rad). The plate was incubated for two hours in a $CO_2$ incubator ($CO_2$ concentration, 5%), and post-reaction absorbance was measured as above. Data were graphed out taking the cytokine concentrations on the horizontal axis and the amount of changes in absorbance after 2-hour incubation on the vertical axis (FIGS. 18, 19, and 20).

The responses of the mixed culture against cytokines began at similar concentration (2 pg/mL of hEPO, 200 pg/mL of hTPO, and 2 pg/mL of hG-CSF) and a similar growth activity was detected as in the individual cultures. The growth of the chimeric receptor-expressing cells was specifically induced by corresponding ligands. The parental cell line did not respond to any cytokine, and no growth activity was observed.

INDUSTRIAL APPLICABILITY

According to the screening methods of the present invention, two or more different activities can be simultaneously assayed with the same index. Therefore, the methods of the present invention enables an efficient and rapid screening for a vast number of test samples to isolate substances having biological activities of interest. The methods of the present invention are particularly suited for the screening of ligands that bind to certain receptors, and serves as an important basic technique for the development of novel pharmaceuticals.

The invention claimed is:

1. A method of screening for a ligand that can bind to at least one of two or more kinds of receptors, wherein said method comprises the steps of:
   (i) providing a composition comprising cells transformed with expression vectors encoding two or more kinds of receptors and expressing said two or more kinds of receptors, each of said receptors comprising (a) a common signal-transducing domain derived from a receptor selected from the group consisting of hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, cell adhesion receptor family, and hormone receptor family, and (b) a ligand-binding domain derived from a receptor selected from the group consisting of hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, cell adhesion receptor family, and hormone receptor family, wherein in each of said kinds of receptors, said ligand-binding domain derives from a different receptor, and binding of a ligand to the ligand-binding domain induces signal transduction through the signal-transducing domain;
   (ii) contacting a test sample with said composition comprising cells expressing two or more kinds of receptors; and
   (iii) detecting binding of said test sample to at least one of said two or more kinds of receptors by detecting a change in a detection marker selected from the group consisting of proliferation activity of the cells, phosphorylation of the receptor or downstream substrate proteins, dephosphorylation of the receptor or downstream substrate proteins, change in cAMP level, change in $Ca^{2+}$ level, and induction of downstream gene expression, wherein said change is induced by signal transduction through said common signal-transducing domain.

2. The method according to claim 1, wherein the cells in the composition comprise two or more kinds of cells, each kind of cell expressing at least one of said two or more kinds of receptors.

3. The method according to claim 1, wherein said signal-transducing domain is derived from a receptor selected from the group consisting of human or mouse erythropoietin (EPO) receptor, human or mouse granulocyte-colony stimulating factor (G-CSF) receptor, human or mouse thrombopoietin (TPO) receptor, and human or mouse epidermal growth factor (EGF) receptor, and wherein said ligand-binding domain is derived from a receptor selected from the group consisting of human or mouse EPO receptor, human or mouse G-CSF receptor, human or mouse TPO receptor, human or mouse insulin receptor, human or mouse Flt-3 receptor, human or mouse platelet-derived growth factor (PDGF) receptor, human or mouse interferon (IFN)-α or -β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor.

4. The method according to claim 3, wherein said signal-transducing domain derives from mouse G-CSF receptor.

5. The method according to claim 1, wherein said cells are derived from a cytokine-dependent cell.

6. The method according to claim 5, wherein said cells are derived from a Ba/F3 cell or a FDC-P1 cell.

7. The method according to claim 1, which method further comprises the step of contacting the test sample with one of said two or more receptors provided in (i) in order to determine the specificity of binding of the test sample.

8. The method of claim 1, wherein, in at least two of said two or more kinds of receptors, said ligand-binding domain derives from a receptor different from the receptor from which the common signal-transducing domain of (i)(a) is derived.

9. A method of identifying a ligand that can bind to at least one of two or more kinds of receptors, wherein said method comprises the steps of:
   (i) providing a composition comprising cells expressing two or more kinds of chimeric receptors, each of said chimeric receptors comprising:
      (a) a common signal-transducing domain derived from a receptor selected from the group consisting of hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, cell adhesion receptor family, and hormone receptor family, and
      (b) an extracellular domain or ligand-binding portion thereof derived from a receptor selected from the group consisting of hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, cell adhesion receptor family, and hormone receptor family, wherein, in each kind of chimeric receptor, said extracellular domain or ligand-binding portion thereof derives from a different receptor, and binding of a ligand to the extracellular domain or ligand-binding portion thereof induces signal transduction through the signal-transducing domain, (ii) contacting said composition with a test sample, and (iii) detecting binding of said test sample to at least one of said two or more kinds of receptors by detecting a change in a detection marker selected from the group consisting of proliferation activity of the cells, phosphorylation of the receptor or downstream substrate proteins, dephosphorylation of the receptor or downstream substrate proteins, change in cAMP level, change in $Ca^{2+}$ level, and induction of downstream gene expression, wherein said change is induced by signal transduction through said common signal-transducing domain.

10. The method of claim 1, wherein said common signal-transducing domain is derived from a receptor selected from the group consisting of EPO receptor, G-CSF receptor, TPO receptor, and EGF receptor.

11. The method of claim 1, wherein the ligand-binding domain of each of said two or more kinds of receptors is derived from a receptor selected from the group consisting of EPO receptor, G-CSF receptor, TPO receptor, insulin receptor, Flt-3 receptor, PDGF receptor, interferon (IFN)-α or β-receptor, leptin receptor, GH receptor, IL-10 receptor, IGF-I receptor, LIF receptor, and CNTF receptor.

12. The method of claim 1, wherein in step (iii), detecting of binding of said test sample to at least one of said two or more kinds of receptors is by detecting a change in proliferation activity of the cells, wherein said change is induced by signal transduction through said common signal-transducing domain.

13. A method of screening for a ligand that can bind to at least one of two or more kinds of receptors, wherein said method comprises the steps of:

(i) providing a composition comprising cells expressing two or more kinds of receptors, each of said receptors comprising (a) a common signal-transducing domain derived from a receptor selected from the group consisting of EPO receptor, G-CSF receptor, TPO receptor, and EGF receptor, and (b) a ligand-binding domain derived from a receptor selected from the group consisting of EPO receptor, G-CSF receptor, TPO receptor, insulin receptor, Flt-3 receptor, PDGF receptor, IFN-α or -β receptor, GH receptor, IL-10 receptor, IGF-I receptor, LIF receptor, and CNTF receptor, wherein in each of said kinds of receptors, said ligand-binding domain derives from a different receptor, and binding of a ligand to the ligand-binding domain induces signal transduction through the signal-transducing domain;

(ii) contacting a test sample with said composition comprising cells expressing two or more kinds of receptors; and (iii) detecting binding of said test sample to at least one of said two or more kinds of receptors by detecting a change in proliferation activity of the cells, wherein said change is induced by signal transduction through said common signal-transducing domain.

14. A method of identifying a ligand that can bind to at least one of two or more kinds of receptors, wherein said method comprises the steps of:

(i) providing a composition comprising cells expressing two or more kinds of chimeric receptors, each of said chimeric receptors comprising:

(a) a common signal-transducing domain derived from a receptor selected from the group consisting of EPO receptor, G-CSF receptor, TPO receptor, and EGF receptor, and (b) an extracellular domain or ligand-binding portion thereof derived from a receptor selected from the group consisting of EPO receptor, G-CSF receptor, TPO receptor, insulin receptor, Flt-3 receptor, PDGF receptor, IFN-α or β-receptor, leptin receptor, GH receptor, IL-10 receptor, IGF-I receptor, LIF receptor, and CNTF receptor, wherein, in each kind of chimeric receptor, said extracellular domain or ligand-binding portion thereof derives from a different receptor, and binding of a ligand to the extracellular domain or ligand-binding portion thereof induces signal transduction through the signal-transducing domain, (ii) contacting said composition with a test sample, and (iii) detecting binding of said test sample to at least one of said two or more kinds of receptors by detecting a change in proliferation activity of the cells, wherein said change is induced by signal transduction through said common signal-transducing domain.

* * * * *

UNITED STATES PATENT AND TRADEMARK OFFICE
CERTIFICATE OF CORRECTION

PATENT NO. : 7,732,133 B2
APPLICATION NO. : 10/333103
DATED : June 8, 2010
INVENTOR(S) : Naohiro Yabuta et al.

It is certified that error appears in the above-identified patent and that said Letters Patent is hereby corrected as shown below:

Column 7, line 4:
 delete "(rFN)-α or -β" and replace with --(IFN)-α or -β--.

Column 23, line 32:
 delete "10 mm" and replace with --10 min--.

Signed and Sealed this

Twenty-first Day of September, 2010

David J. Kappos
*Director of the United States Patent and Trademark Office*